(12) United States Patent
Arbel et al.

(10) Patent No.: US 12,138,452 B2
(45) Date of Patent: Nov. 12, 2024

(54) NON-INVASIVE DEVICE AND METHOD FOR TREATING THE DIGESTIVE SYSTEM AND FOR SYNCHRONIZING STIMULATION WITH BREATH

(71) Applicant: GerdCare Medical Ltd., Yokneam Illit (IL)

(72) Inventors: Giora Arbel, Tel Mond (IL); Mordechay Esh, Givatayim (IL)

(73) Assignee: GerdCare Medical Ltd., Yokneam Illit (IL)

( * ) Notice: Subject to any disclaimer, the term of this patent is extended or adjusted under 35 U.S.C. 154(b) by 713 days.

(21) Appl. No.: 17/287,199

(22) PCT Filed: Oct. 10, 2019

(86) PCT No.: PCT/IB2019/058633
§ 371 (c)(1),
(2) Date: Apr. 21, 2021

(87) PCT Pub. No.: WO2020/084372
PCT Pub. Date: Apr. 30, 2020

(65) Prior Publication Data
US 2022/0023628 A1    Jan. 27, 2022

Related U.S. Application Data

(60) Provisional application No. 62/748,468, filed on Oct. 21, 2018.

(51) Int. Cl.
*A61N 1/36* (2006.01)
*A61B 5/282* (2021.01)
(Continued)

(52) U.S. Cl.
CPC .......... *A61N 1/36007* (2013.01); *A61B 5/282* (2021.01); *A61B 5/304* (2021.01);
(Continued)

(58) Field of Classification Search
CPC . A61N 1/36031; A61N 1/0452; A61N 1/0484
See application file for complete search history.

(56) References Cited

U.S. PATENT DOCUMENTS

| 5,716,385 A | 2/1998 | Mittal et al. |
| 6,097,984 A | 8/2000 | Douglas |

(Continued)

FOREIGN PATENT DOCUMENTS

| EP | 1272250 A1 | 1/2003 |
| EP | 1480283 A1 | 8/2012 |

(Continued)

OTHER PUBLICATIONS

International Search Report.
International Written Opinion.
European Search Report.

*Primary Examiner* — Eric D. Bertram
(74) *Attorney, Agent, or Firm* — Rivka Friedman

(57) ABSTRACT

A noninvasive ergonomic self-use device including a plurality of electrodes and a processor in electrical communication with the electrodes, the processor is configured to switch two or more of the electrodes between at least an ECG mode of operation in which the electrodes receive user body signals and an EPG mode in which the electrodes generate electrical pulses for stimulating the abdominal muscles of the user.

11 Claims, 16 Drawing Sheets

(51) Int. Cl.
*A61B 5/304* (2021.01)
*A61N 1/04* (2006.01)
*G16H 20/30* (2018.01)
*G16H 40/63* (2018.01)

(52) U.S. Cl.
CPC ......... *A61N 1/0452* (2013.01); *A61N 1/0456* (2013.01); *A61N 1/0484* (2013.01); *A61N 1/36031* (2017.08); *G16H 20/30* (2018.01); *G16H 40/63* (2018.01)

(56) References Cited

U.S. PATENT DOCUMENTS

| | | |
|---|---|---|
| 8,538,534 B2 | 9/2013 | Soffer et al. |
| 9,174,046 B2 * | 11/2015 | Francois ............ A61N 1/36014 |
| 9,962,544 B2 * | 5/2018 | Southwell ............ A61N 1/0456 |
| 2006/0155340 A1 | 7/2006 | Schuler et al. |
| 2008/0086179 A1 | 4/2008 | Sharma |
| 2010/0324612 A1 * | 12/2010 | Matos ................... A61N 1/0492 704/235 |
| 2014/0277226 A1 * | 9/2014 | Poore ................... A61N 1/0484 607/7 |
| 2017/0209693 A1 * | 7/2017 | An ....................... A61N 1/0456 |
| 2017/0231490 A1 | 8/2017 | Toth et al. |
| 2018/0214692 A1 * | 8/2018 | Esh ..................... A61N 1/36031 |
| 2020/0179686 A1 * | 6/2020 | Son ...................... A61B 5/0803 |

FOREIGN PATENT DOCUMENTS

| | | |
|---|---|---|
| EP | 3229892 A1 | 10/2017 |
| EP | 1906817 B1 | 1/2019 |
| WO | 2006113802 A2 | 10/2006 |

\* cited by examiner

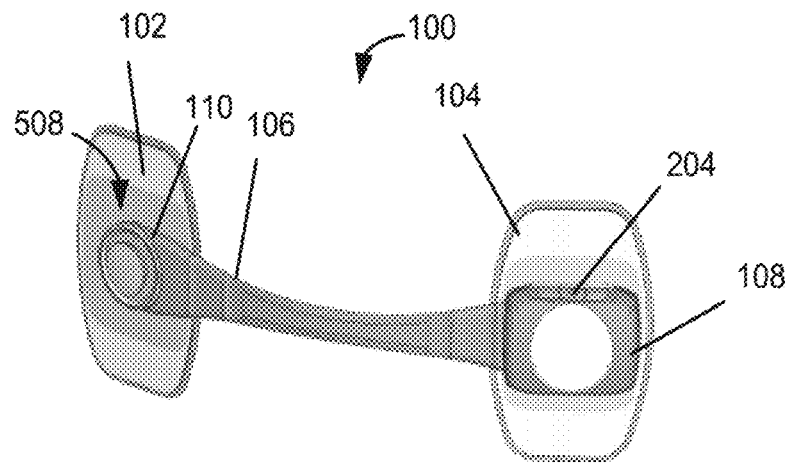
FIG. 1A
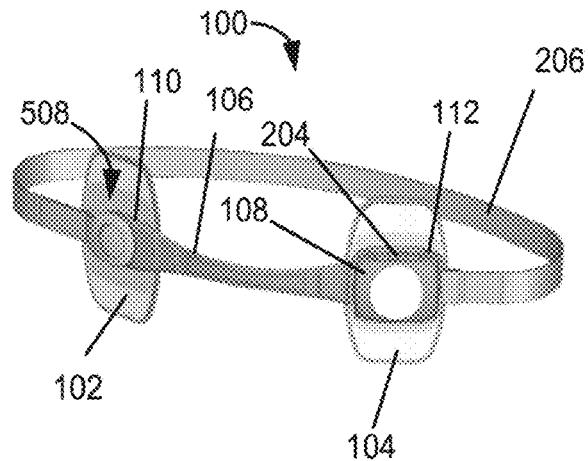
FIG. 1B
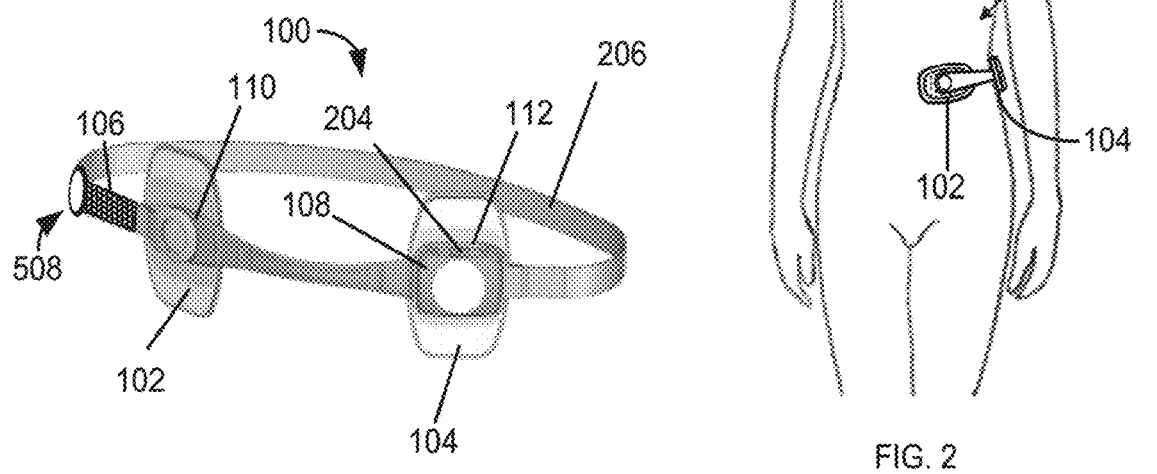
FIG. 1C
FIG. 2

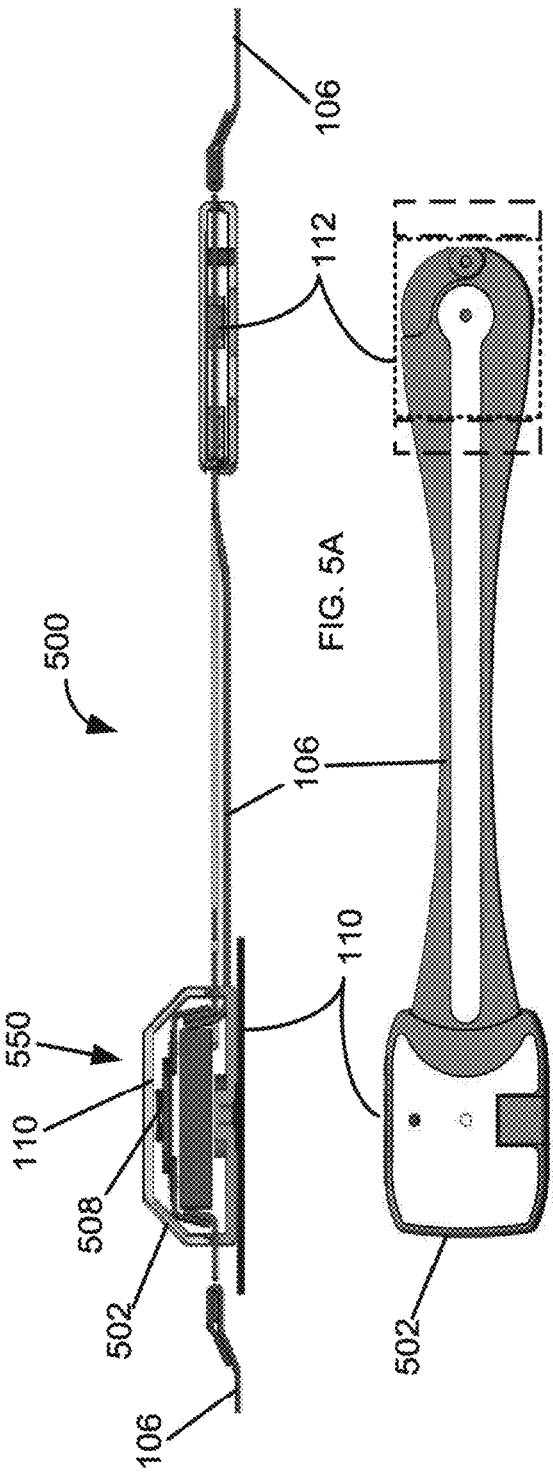
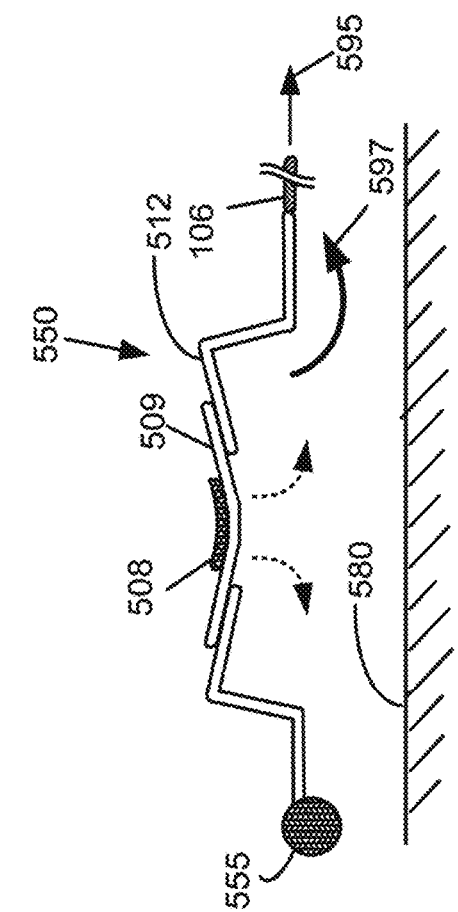
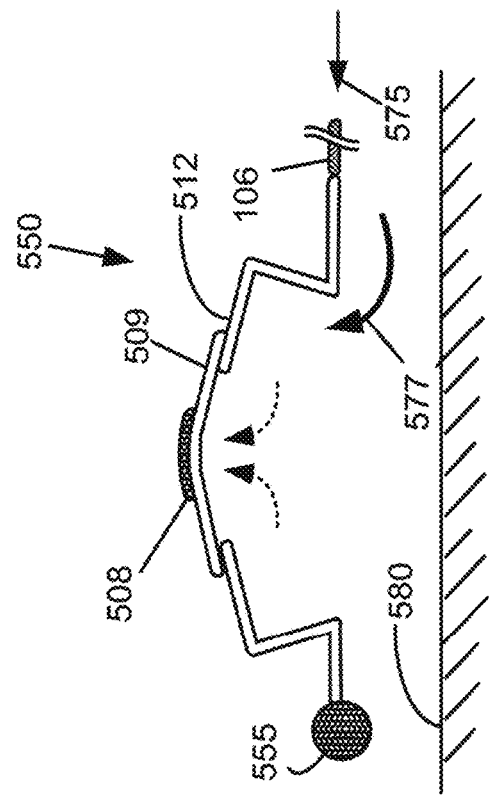
FIG. 5A
FIG. 5B
FIG. 5C

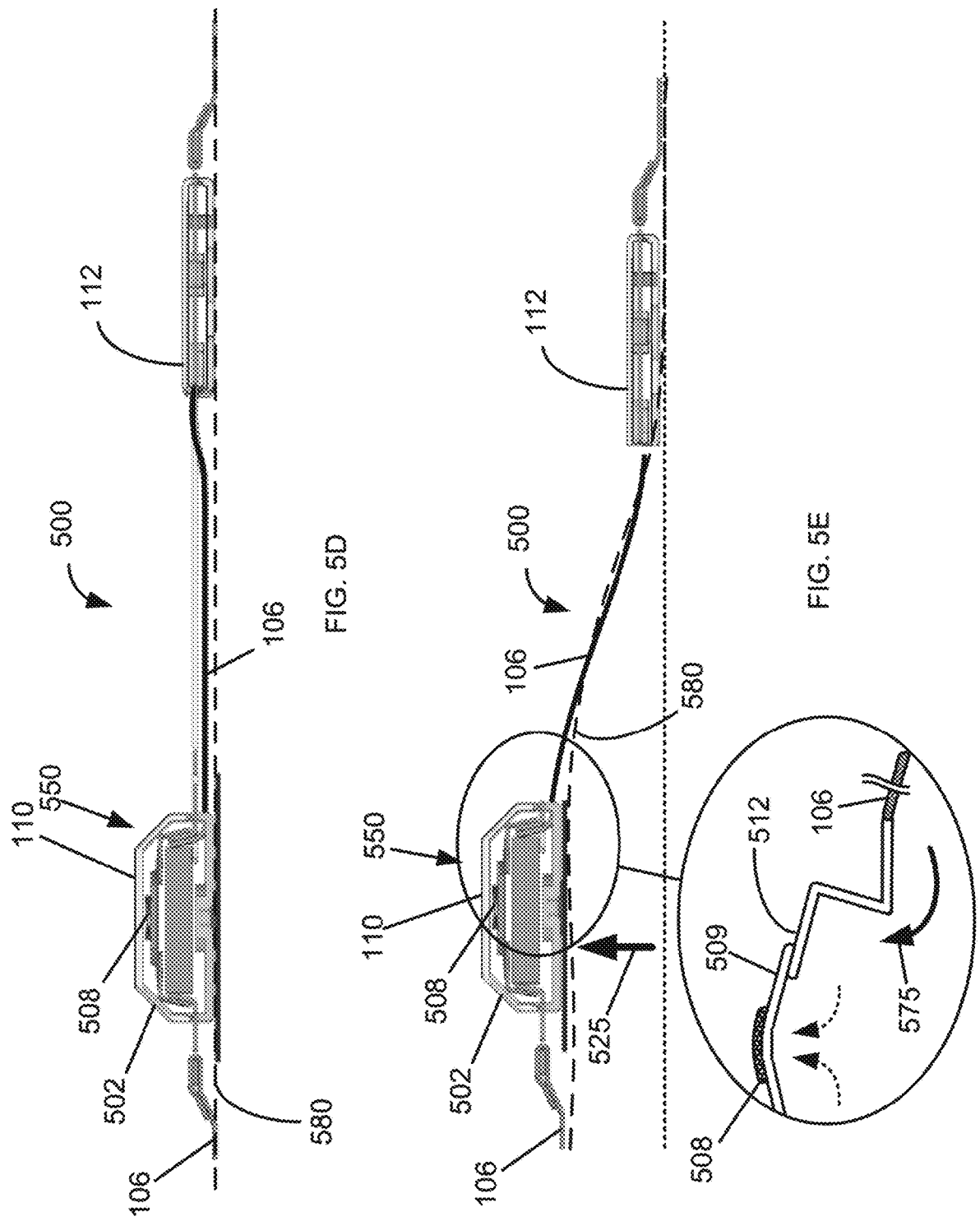

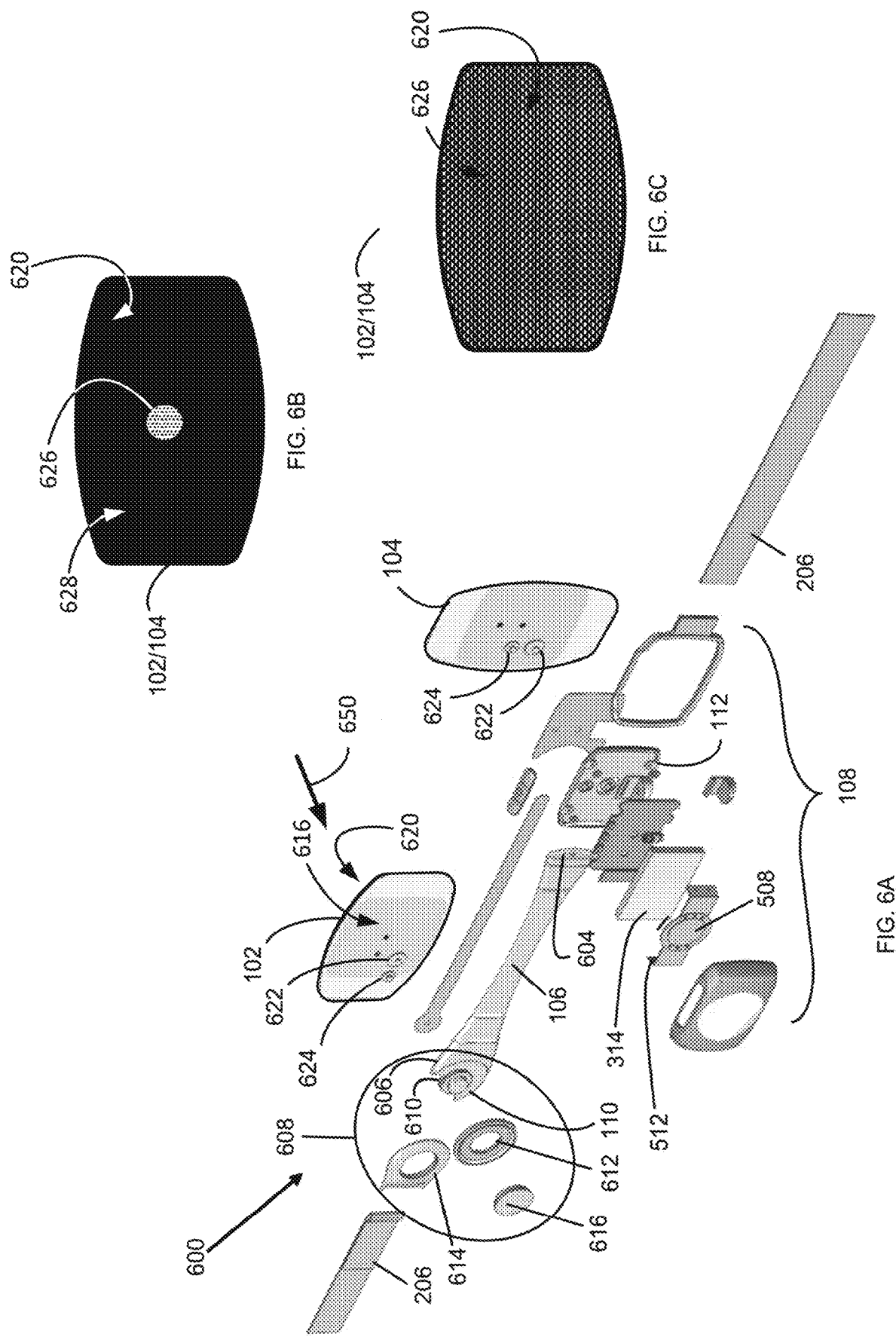

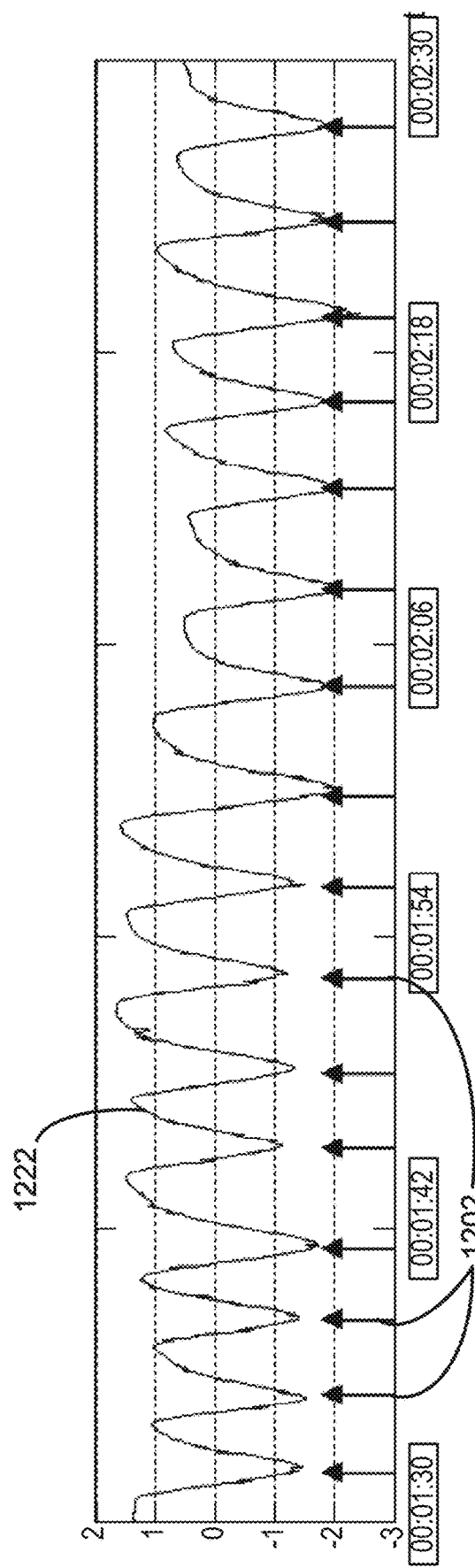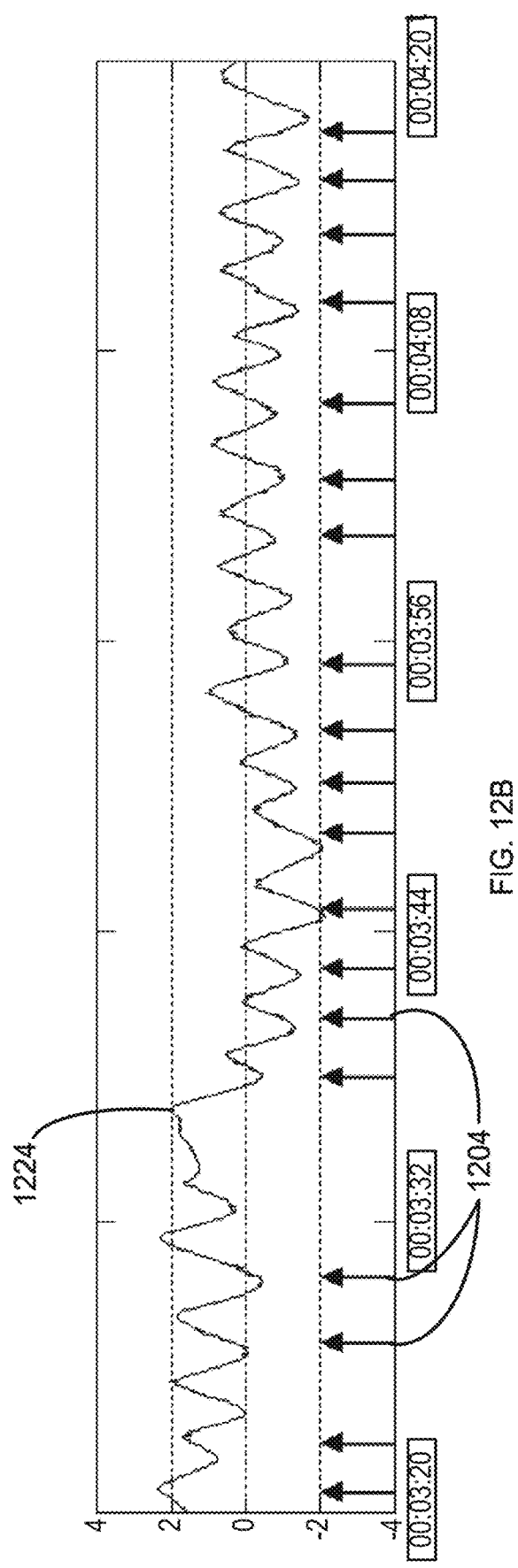
FIG. 12A
FIG. 12B

NON-INVASIVE DEVICE AND METHOD FOR TREATING THE DIGESTIVE SYSTEM AND FOR SYNCHRONIZING STIMULATION WITH BREATH

FIELD OF THE INVENTION

The invention, in some embodiments thereof, relates to medical devices and, more particularly, but not exclusively, to a device and method related to the digestive system.

BACKGROUND

Gastroesophageal reflux disease (GERD) is caused by stomach acid coming up from the stomach into the esophagus. GERD is usually caused by changes in the barrier between the stomach and the esophagus, including abnormal relaxation of the lower esophageal sphincter (LES) (which normally holds the top of the stomach closed), impaired expulsion of gastric reflux from the esophagus, or a hiatal hernia.

Treatment of digestive system diseases, such as Gastroesophageal reflux disease (GERD) is typically via lifestyle changes and medications. Medication therapy is associated with various adverse effects, raising concern about the safety of its long-term use. Surgical therapy and endoscopic interventions provide an alternative to users that do not respond to medication therapy or for users reluctant to use such medications for long periods of time, however, it too is associated with adverse effects.

The foregoing examples of the related art and limitations related therewith are intended to be illustrative and not exclusive. Other limitations of the related art will become apparent to those of skill in the art upon a reading of the specification and a study of the figures.

Background includes U.S. Pat. No. 9,925,375, granted 27 Mar. 2018, entitled "Non-invasive device and method for treating gastro esophageal reflux disease (GERD) and the digestive system"

Background includes the master thesis "Evaluation of Algorithms for ECG Derived Respiration in the Context of Heart Rate Variability Studies" by Lasse Sohrt-Petersen, the Biomedical Engineering and Informatics of Alborg university.

SUMMARY

The following embodiments and aspects thereof are described and illustrated in conjunction with systems, device and methods which are meant to be exemplary and illustrative, not limiting in scope.

One exemplary embodiment of the disclosed subject matter is a non-invasive treatment device, comprising: a plurality of electrodes, and a processor, electrically connected to the electrodes, wherein, the processor is configured for switching at least two of the electrodes between an ECG mode of operation in which the electrodes receive subject body signals, and an EPG mode, in which the electrodes generate electrical pulses for stimulating the abdominal muscles. According to some embodiments the processor is further configured for detecting from ECG signals received from the electrodes inhalation phase and for switching from the ECG mode to the EPG mode as a result of the detecting the inhalation phase. According to some embodiments the detecting comprises utilizing Electrocardiogram Derived Respiration algorithm for the detecting the inhalation phase. According to some embodiments wherein the device is further configured for treating digestive symptoms by the stimulation wherein the digestive symptoms being one member selected from a group consisting of gastroesophageal reflux, obesity and constipation. According to some embodiments the electrodes are configured for being positioned over abdominal muscles at the level of the waistline of the subject. According to some embodiments the processor is further configured for synchronizing the electrical pulses for stimulating the abdominal muscles with inhalation phase of the subject and between heartbeats to avoid loss of ECG data. According to some embodiments the electrodes are dual function for operating EPG mode ECG mode. According to some embodiments the device further comprising an ECG circuit connectable to the electrodes, wherein the switching to the EPG mode of operation comprises disconnecting the ECG circuit from the electrodes and wherein the switching to the ECG mode comprises reconnecting the ECG circuit to the electrodes. According to some embodiments the processor is configured to switch from the EPG mode of operation to ECG mode of operation in between bursts of pulses. According to some embodiments the device comprises one or more accelerometer or a gyro unit electrically connected to the processor; wherein the acetometer or the gyro unit is configured to adjust the stimulation intensity according to the body position and body activity. According to some other embodiments The processor is configured to measure muscles response to stimulation and adjust stimulation parameters to generate stable muscle movement One other exemplary embodiment of the disclosed subject matter is non-invasive treatment device, comprising: An ECG sensor, the ECG sensor comprises a plurality of electrodes configured to be position in an abdomen area of a subject, wherein the electrodes are configured for monitoring ECG signals of the subject and for applying stimulation on muscles of the abdomen area; a Piezoelectric sensor configured to generate a second signals in accordance with variations in the girth and position of the abdomen area; and a processor, electrically connected to the electrodes; wherein, the processor is configured for measuring a first variation of time of breathing of the subject detected from the ECG sensor and for measuring a second variation of time of breathing of the subject detected from the Piezoelectric sensor; for selecting a sensor associated with lowest variation from the first variation and form the second variation and for the applying the simulation according to inhalation phase detected by the selected sensor. According to some embodiments the device further comprising a band, wherein the band interconnecting the Piezoelectric sensor and at least one electrode base of the plurality of electrodes and is configured for transferring motion of the abdomen between the Piezoelectric sensor and the at least one electrode base during inhalation or during exhalation for the detecting the second inhalation phase. According to some embodiments the electrodes comprises magnetic studs; the magnetic male studs attract to female snaps that are mounted into a plastic base for maintaining proper mechanical and conductive coupling.

One exemplary embodiment of the disclosed subject matter is a device, comprising: a plurality of electrodes configured to be position in an abdomen area of a user; a Piezoelectric sensor configured to generate a second signal in accordance with variations in the girth and position of the abdomen area; and a band wherein the band interconnecting the Piezoelectric sensor and at least one electrode base of the plurality of electrodes and is configured for transferring motion of the abdomen between the Piezoelectric sensor and the at least one electrode base during inhalation or during exhalation for monitoring inhalation of the user.

According to some embodiments the electrodes comprises magnetic studs; the magnetic male studs attract to female snaps that are mounted into a plastic base for maintaining proper mechanical and conductive coupling.

One exemplary embodiment of the disclosed subject matter is a device comprising: two tense electrodes, wherein the electrodes are configured for being positioned in abdomen area of a user; an non grounded ECG amplifier in connectivity with the electrodes configured for amplifying ECG signal and a processor, electrically connected to the electrodes, wherein the processor is configured for receiving user body signals from the electrodes, for calculating ECG result from the signals and for transferring the ECG result to an application.

According to an aspect of some embodiments of the invention there is provided a non-invasive device and method for treating gastro esophageal reflux disease (GERD) and the digestive system (hereinafter: "The Device"). In some embodiments, the device is configured to affect the abdominal muscles. In some embodiments, the abdominal muscles in turn promote digestive system activity (e.g., contractions and/or motility). In some embodiments, the abdominal muscles are affected by electrical pulses applied by electrodes. In some embodiments, the generation of electrical pulses is synchronized with a certain phase of the respiration cycle (e.g., inhalation). In some embodiments, the device comprises a Piezoelectric element configured to generate signals in accordance with variations in the girth of the abdomen area and spatial position and orientation of the electrodes in respect to each other during the respiration cycle. In some embodiments, the Piezoelectric element is mounted at an end of a semi-rigid system or rigid system mount. In some embodiments, the mount is coupled to at least one electrode basis. In some embodiments, the mount is coupled between the two electrode basses. In some embodiments, the mount is coupled to the device control box. In some embodiments, the mount is coupled to a belt.

In some embodiments, the pulse generation is synchronized with a specific phase of the respiration cycle. In some embodiments, the pulse generation is synchronized with the inhalation phase of the respiration cycle. In some embodiments, information regarding phases of the respiration cycle is derived from an ECG analysis.

In some embodiments, the device generates electrical pulses. In some embodiments, the pulses are synchronized with body signals. In some embodiments, body signals comprise chest movement associated with breathing, abdominal movement, associated with breathing, ECG, thorax impedance, oximeter readings, body movements (accelerometer) and body position. In some embodiments, the electrical pulses are applied during the inhalation phase of the respiratory cycle.

According to an aspect of some embodiments of the invention there is provided, the device, comprising: two or more electrodes, and a processor, electrically connected to the electrodes. The processor is configured to switch the electrodes between an ECG mode of operation in which the electrodes monitors ECG signals, and a stimulating mode, in which the electrodes generate electrical pulses for stimulating the abdominal muscles.

In some embodiments, the device comprises a processor with an EDR (Electrocardiogram Derived Respiration) algorithm configured to derive from ECG signals the phases of the respiration cycle.

In some embodiments, the processor is configured to switch between modes of operation, e.g., electrical pulse generation and ECG monitoring, in synchronization with the phases of the respiration cycle. According to some embodiments, the electrodes are configured to receive ECG signals and/or transmit stimulating pulses in synchronization with an increase of pressure applied to the digestive system during inhalation.

In some embodiments, the device comprises at least a first pair of electrodes configured to monitor ECG signals and a second pair of electrodes configured to apply electrical pulses that affect the abdominal muscles.

In some embodiments, the electrodes comprise an adhesive surface (e.g., conductive hydrogel) configured to adhere the electrodes to skin.

According to an aspect of some embodiments of the invention there is provided the device, comprising: two or more electrodes for stimulating the abdominal muscles by transmitting electrical pulses in synchronization with a respiration cycle phase, and the electrodes monitors ECG signals in between transmitting stimulating electrical pulses.

According to some embodiments, the electrical device comprises a processor that controls activation and/or termination of the electrical pulses. In some embodiments, the processor is configured to run an algorithm for identifying the respiration phase derived from ECG signals e.g., ECG-derived respiration (EDR).

According to an aspect of some embodiments of the invention there is provided the device, comprising: a Piezoelectric (PE) element for generating signals in accordance with changes of the girth of the abdomen area of the user, during the respiration cycle, and two or more stimulating electrodes for stimulating the abdominal muscles of a user by transmitting electrical pulses in synchronization with the Piezoelectric element signals. In some embodiments, the Piezoelectric (PE) element is configured to generate signals in accordance with changes a position of the two or more electrodes in respect to one another and/or in respect to the PE element.

In some embodiments, the changes of the girth of the abdomen area detected by the Piezoelectric element are of one or more transitional stages in between respiration cycle phases. According to some embodiments, the electrode bases are connected to the Piezoelectric sensor, so that signals of the Piezoelectric element correspond to a relative motion of the electrode bases in respect to the Piezoelectric sensor. In some embodiments, the relative motion corresponds to the respiration cycle phases.

According to some embodiments, the device comprises a band interconnecting the Piezoelectric (PE) element and at least one electrode base. In some embodiments, the band is axially non-extendable and non-compressible and configured to transfer relative motion between the PE sensor and one or more electrode bases during inhalation and/or during exhalation. In some embodiments, the band is rigid.

In addition to the exemplary aspects and embodiments described above, further aspects and embodiments will become apparent by reference to the figures and by study of the following detailed description.

One technical problem disclosed by the present disclosure is how to optimize the synchronization between the stimulation pulses and the breath of the patient. The synchronization is required for generating pulses only while the abdomen pressure is positive (or rigid) through the inspiration cycles.

One technical solution is to detect the breathing phase simultaneously by a Piezoelectric sensor via LP (Low Pass)

filter (defined as Piezo Mode) and by the EDR (ECG Derived Respiration) method (defined as ECG Mode) and to select the most performing mode for determining the time of a next series of stimulation pulses. According to some embodiments the device determines the inhalation phase per stimulation either by the ECG Mode or by the Piezo mode. According to some embodiments each sensor (ECG sensor and Piezo sensor) outputs the time of breathing in each inhalation cycle. The device calculates the deviation between consecutive measures per each sensor for a certain time period. In one example the certain time period is 10 seconds. The device selects the more stable sensor for determining the inhalation period, for synchronizing the stimulation with the inhalation period.

A stable mode is a mode in which the average deviation between consecutive measured time of breathing in a certain time interval cycle is minimal. Usually at rest the Piezo Mode is more stable however in motion, the Piezo Mode becomes noisy due to combined body motions; thus, in motion the ECG mode typically becomes more stable and causing the device to change the mode accordingly.

One other technical problem is how to utilize the stimulation electrodes for measuring ECG signals. Such utilization enables to measure the ECG from a belt that is placed in the hip of the patient without the need for placing the electrodes that are typically used by a conventional ECG device.

One other technical solution is to implement single channel ECG which utilizes only two large size electrodes that are used for the stimulation, thus simplifying the use of the device. Typically, ECG requires a third ground electrode, however the system is floated (e.g. isolated from any conductive element).

The accelerometer functions:
1. Body position detection enables adjustment the stimulation intensity according the body position.
2. Body activity (like walking, running) detection enables adjustment the stimulation intensity according the body activity.
3. Enables the piezo synchronization to breathing cycle.
4. Measure the muscles response to the stimulation than the device can generate stable muscle movements.

According to some embodiments the device, uses the ECG data for EDR algorithm. The device is connected to the application wirelessly via BLE communication and is small in size as required to minimize interference from noisy environment, therefore good ECG signals can be monitored without the ground electrode.

Since there is large difference between the input of the ECG amplifier (order of a few mV) and the stimulation output (of about 120V-300V), both use the same electrodes, it is required to protect the ECG amplifier from the high voltage of the stimulation and the charge remained in the electrode after the end of the simulation burst. Protecting is achieved by disconnecting the ECG via a pair of Optocouplers (controlled by the main processor) and discharging the electrode by shorting for a short time (0.5-5 mS) following the end of the burst.

BRIEF DESCRIPTION OF THE FIGURES

Exemplary embodiments are illustrated in referenced figures. Dimensions of components and features shown in the figures are generally chosen for convenience and clarity of explanation and are not necessarily shown to scale. The figures are listed below.

FIGS. 1A, 1B and 1C, are perspective view simplified illustrations of an electrical device (hereinafter: The device) in accordance with some embodiments of the invention;

FIG. 2 is a plan view simplified illustration of positioning of the device on a human body in accordance with some embodiments of the invention;

FIGS. 5A, which is a plan view and a Cross section view simplified illustration of the device PE sensor mounted on an electrode base interconnecting band in accordance with some embodiments of the invention;

FIGS. 5B, 5C, 5D and 5E, which are view simplified illustrations of the device PE sensor in accordance with some embodiments of the invention;

FIGS. 6A, 6B and 6C are an exploded view and plan view simplified illustrations of the device and electrode skin-contacting surfaces in accordance with some embodiments of the invention;

FIGS. 12A and 12B are graphs of triggers positions obtained from input from a piezoelectric element sensor in rest (12A) and in the movement time (12B);

FIGS. 14A, 14B, 14C, 14D and 14E illustrate exemplary screen shots of an application for operation, control physiological parameters report of the disclosed device.

DETAILED DESCRIPTION

Figure 3A:
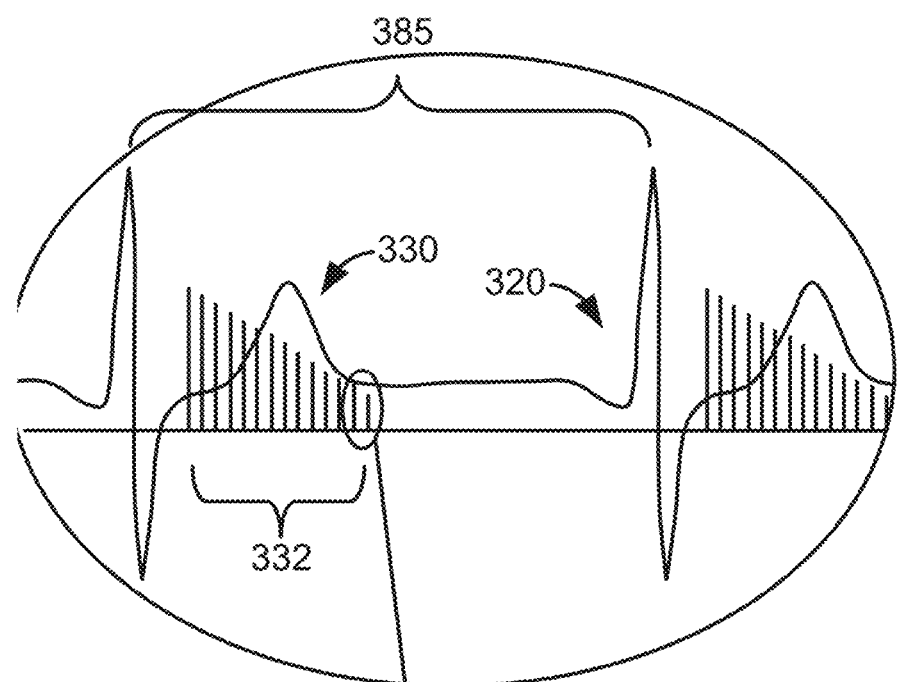
FIGS. 3A and 3B and 3C are simplified graphs superimposing an electrocardiogram output and respiration waveform monitored by the device in accordance with some embodiments of the invention.

Embodiments of the invention disclose a noninvasive ergonomic self-use device for facilitating therapy of gastrointestinal system diseases or symptoms, for example Gastroesophageal Reflux Disease (GERD), obesity and constipation. The device is adapted to be positioned on the skin of the user abdomen and generate electrical pulses that affect the abdominal muscles, which in turn apply intra-abdominal pressure that affects esophageal emptying and/or inhibits gastric reflux and abates gastroesophageal reflux symptoms.

In some embodiments, the electrical pulses are synchronized with the user body signals. For example, the pulses may be synchronized with the breathing cycle, heart rate—ECG reading, monotony movements, and body position. Synchronizing may be done by sensors that are included in the device. In some cases, breathing and body position change the stomach and esophagus pressure and position. In some embodiments, the electrical pulses are synchronized with the respiratory cycle and generate pulses only when the abdominal pressure associated with the respiration cycle is positive, i.e., during inspiration. In some embodiments, e.g. for the treatment of GERD, the electrical pulses are generated when abdominal pressure increases and are terminated when the abdomen pressure decreases.

According to an aspect of some embodiments of the invention there is provided the device. In some embodiments, the device comprises a plurality of electrodes configured to generate electrical pulses. In some embodiments, the electrodes are configured to receive ECG signals. In some embodiments, the electrodes are dual-function (e.g., TENS/ECG monitoring) electrodes.

In some embodiments, the device comprises a processor configured to switch the electrodes mode of function from an ECG signal receiving mode (ECG mode) and an electrical pulse generating mode (EPG mode). In some embodiments, the device processor is configured to switch the electrodes mode of function from a pulse generating mode to an ECG signal receiving mode between bursts of electrical pulses. In some embodiments, the device processor is configured to switch the electrodes mode of function from an electrical pulse generating (EPG) mode to an ECG signal receiving mode (ECG mode) between individual pulses within one or more bursts of pulses.

According to some embodiments, the processor is configured to switch between the EPG (an electrical pulse generating mode) and ECG (Electrocardiograph) modes in synchronization with a respiration cycle phase. In some embodiments, the processor is configured to analyze ECG signals from the electrodes and derive from the ECG analysis the respiration cycle waveform over a given period of time. In some embodiments, the processor is configured to identify from the derived waveform a respiratory phase of the respiratory cycle at any given time. In some embodiments, the processor is configured to synchronize the generation of stimulating pulses with an increase or a decrease of a pressure applied by the abdominal muscles on the digestive system (e.g. stomach, esophagus) during the respiration cycle. In some embodiments, the processor is configured to control parameters of the stimulating electrical pulses, such as: frequency, amplitude, wave forms, and current.

In some embodiments, the electrodes comprise an adhesive surface (e.g., adhesive hydrogel) and are attached by adhesion to the body. In some embodiments, the device is applied to a user's body solely by adhesion with no other support (e.g., belt or harness). In some embodiments, the device comprises at least one belt for securing the device over the abdomen area.

According to an aspect of some embodiments of the invention, the synchronizations between stimulation and breath may be used by a method for promoting digestive tract activity (e.g., contraction and/or motility). In some embodiments, the method comprises stimulating the abdominal muscles. In some embodiments, the method comprises attaching a plurality of electrodes to a body of a user at the level of the umbilicus. In some embodiments, the method comprises acquiring one or more respiration cycle waveforms and identifying at least the inhalation phase of the respiratory cycle. In some embodiments, generating one or more electrical pulses from two or more electrodes during the inhalation phase of the respiratory cycle. In some embodiments, the method comprises acquiring ECG signals. In some embodiments, acquiring one or more respiration cycle waveforms and identifying at least the inhalation phase of the respiratory cycle using the EDR (Electrocardiogram Derived Respiration) technique. In some embodiments, the method comprises acquiring ECG data in between the generated stimulating electrical pulses. According to an aspect of some embodiments of the invention the electrical device comprises a Piezoelectric element configured to generate signals in accordance with variations in the girth of the abdomen area during the respiration cycle and change of spatial position and orientation of the electrodes in respect to each other. In some embodiments, the Piezoelectric element detects transitional stages in between the respiration cycle phases, for example a beginning of an inhalation and/or an exhalation. In some embodiments, the Piezoelectric element is mounted at an end of a semi-rigid or rigid mount. In some embodiments, the mount is coupled between at least two electrode bases. In some embodiments, the mount is coupled to a device control box. In some embodiments, the mount is coupled to a belt.

According to some embodiments, the device comprises a band interconnecting the Piezoelectric element and at least one electrode base. In some embodiments, the band is configured to transfer a relative motion between the electrode base and the Piezoelectric element throughout a complete respiratory cycle (during inhalation and during exhalation). In some embodiments, the band is axially non-extendable and non-compressible. In some embodiments, the band is rigid. In some embodiments, the band comprises a portion of a belt.

Reference is now made to FIGS. 1A, 1B, 1C and 2, which are perspective view and plan view simplified illustrations of the device and implementation of the device in accordance with some embodiments of the invention. As shown in FIG. 1A, the electrical device 100 comprises two or more electrodes 102 and 104 mounted on electrode bases 110/112 respectively coupled to opposite ends of a connecting band 106. In some embodiments, surfaces of at least one of electrodes 102/104 are coated with a biocompatible adhesive (e.g., conductive hydrogel) hydrogel 628 configured to enable multiple use of one or more electrodes 102/104 to skin without additional support e.g., with a belt. In some embodiments, one or more bases 110/112 comprise a portion of band 106. In some embodiments, electrodes 102/104 are dual-function (e.g., EPG/ECG monitoring) electrodes. The EPG function comprises generating abdominal muscles stimulating pulses and the ECG function monitoring body ECG signals. The EPG/ECG monitoring functions of electrodes 102/104 alternate over a set period of time as explained in greater detail elsewhere herein.

In some embodiments, device 100 comprises a control box 108 that houses electrical components e.g., processor circuit boards, switches, voltage booster and at least a processor 202 (FIG. 4A). In some embodiments, processor 202 is in electrical and/or data communication with electrodes 102/104. As explained in greater detail elsewhere herein, in some embodiments, processor 202 is configured to switch electrodes 102/104 between at least an ECG mode of operation and an EPG mode. When set to an ECG mode, the electrodes monitor body ECG signals and when set to an EPG mode, the electrodes generate electrical pulses for stimulating the abdominal muscles, which in turn promote digestive tract activity. In some embodiments, the device comprises separate ECG mode of operation electrodes and EPG mode of operation electrodes. In some embodiments, electrodes 102/104 are disposable.

According to some embodiments, device 100 comprises a band 106 interconnecting electrode bases 110/112 at ends 606 and 604 respectively (FIG. 6A). In some embodiments, the band 106 transfers a relative motion between electrode bases 110/112 generated by expansion and contraction of the chest and/or abdominal muscles during a respiratory cycle (inhalation and exhalation). In some embodiments, electrodes 102/104 with control box 108 are in electrical and data communication via at least one electrical and data conduit within band 106.

According to some embodiments the electrical device 100 comprises a plurality of control buttons 204. In some embodiments, the control buttons 204 enable manual activation or termination of the stimulating pulses. In some embodiments, activation is automatic by tension applied by band 106 on a piezoelectric (PE) element coupled to one end of band 106. In some embodiments, device 100 is activated by an application on a mobile device (e.g., smart phone, smart tablet or laptop computer).

As shown in the exemplary embodiment depicted in FIG. 2, the generation of stimulating electrical pulses at the flank area of the body, over the Rectus Abdominis and the External Oblique muscles, provides the most effective response of the digestive tract and primarily the esophagus and stomach, to device 100.

As shown in FIG. 2, which is a perspective view simplified illustration of implementation of the device of FIG. 1A, the authors of this disclosure have found that positioning of the pulse emitting electrodes (e.g., 102/104) over the abdominal muscles at the level of the waist line of a subject, e.g., over the Rectus Abdominis and the External Oblique muscles, provides the most effective treatment of the digestive tract. As depicted in the exemplary embodiment shown in FIG. 2, electrode 102 is placed in a horizontal configuration over a lower Rectus Abdominis muscle and electrode 104 is placed in a vertical configuration over a lower Oblique muscle. During the respiratory cycle the movement differential between the Rectus Abdominis muscles and the External Oblique muscles is expressed by variation in tensile/compression forces applied to the PE sensor 508 as explained in greater detail elsewhere herein.

According to some embodiments, one or more of the phases of the respiration cycle is determined by a signal detected by electrodes 102/104. According to some embodiments, electrodes 102/104 transmit stimulating pulses in synchronization with an increase or a decrease in pressure applied on the digestive system (e.g. stomach, esophagus) by the abdominal muscles during the respiration cycle.

Figure 3B:
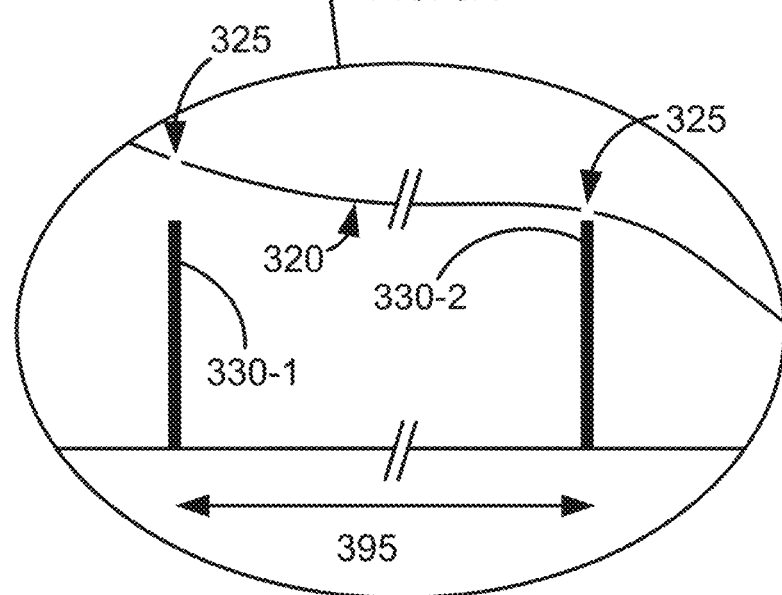
Figure 3C:
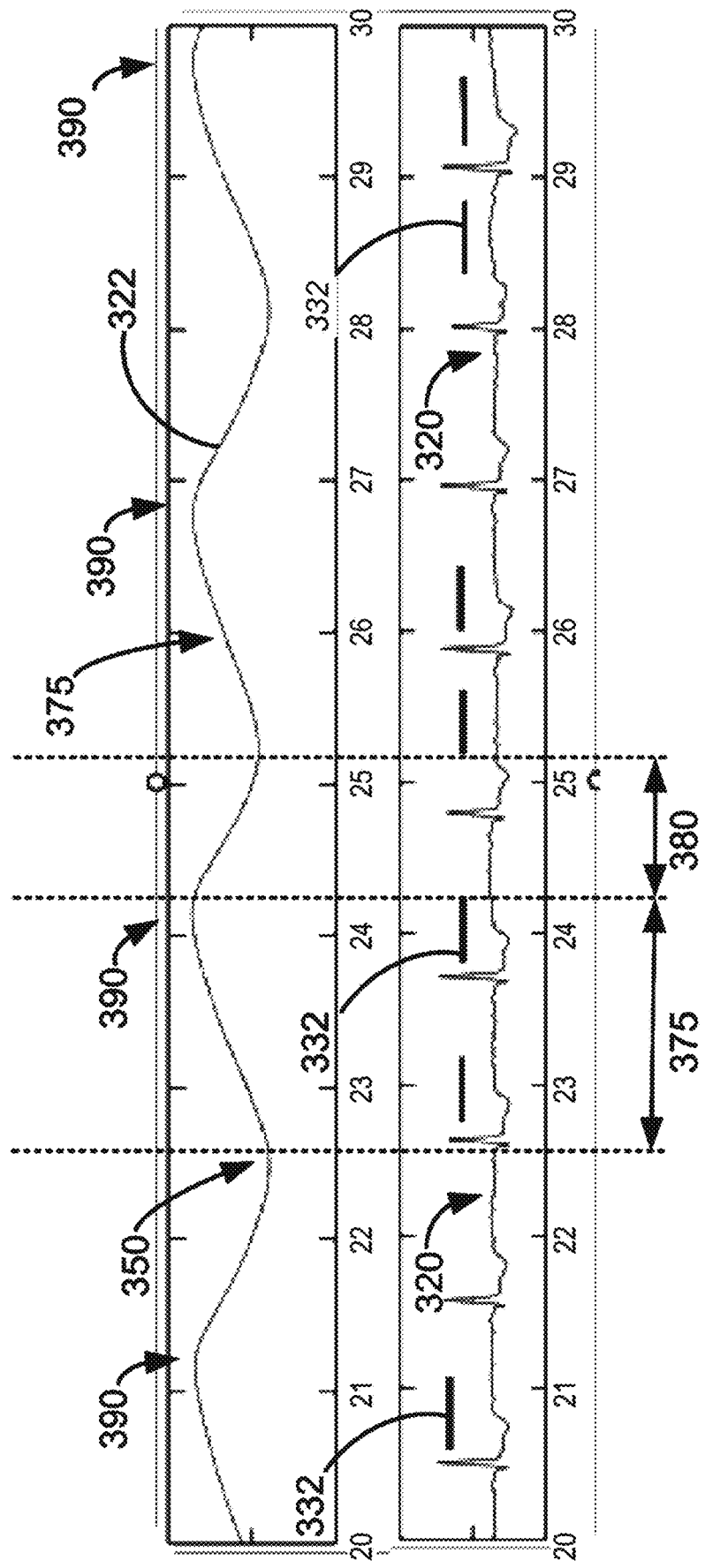

Reference is now made to FIGS. 3A, 3B and 3C, collectively referred to as FIG. 3. FIGS. 3A, 3B are simplified graphs superimposing an electrical stimulating pulse diagram and an ECG reading generated by a processor of the device according to some embodiments of the invention. FIG. 3C is a simplified graph superimposing an electrical stimulating pulse diagram, an ECG reading, and respiration reference monitored by a nasal pressure sensor or a nasal thermistor according to some embodiments of the invention. In some embodiments and as shown in FIGS. 3A and 3B, device 100 processor 202 is configured to sample ECG signals approximately 1000 times per second, on average, the period of time 385 between individual heart beats (e.g., at 60 BPM). In some embodiments, and as depicted in FIG. 3A, electrical pulses 330 are biphasic with a certain time pattern and with an optional modulated pattern. The generated pulses 330 are synchronized with the patient breathing phase and are generated during the inhalation phase, between heartbeats and at a predetermined pattern (e.g., rate and/or duration).

As explained in greater detail elsewhere herein, device 100, electrodes 102/104 are dual-function (e.g., EPG/ECG monitoring) electrodes and are time-shared to generate pulses or read ECG signals. In this configuration, during pulse generation, electrodes 102/104 do not read ECG signals and vice versa. As described elsewhere herein, the ECG is sampled between 200 and 1500 times per second. For example, in some embodiments, the ECG is sampled 1000 samples between heartbeats at a heart rate of 60 BPM. The duration of a single generated pulse is very short (approximately 0.45 mS) in relation to a duration of an ECG cycle 385 (approximately 1 second) hence, the missing ECG input from unread portions 325 in the ECG reading during pulse bursts generation are negligible.

As stated elsewhere herein, in some embodiments, electrodes 102/104 are dual-function (e.g., EPG/ECG monitoring) electrodes. The EPG function comprises generating stimulating electrical digestive system stimulating pulses and the ECG function monitoring body ECG signals. The EPG/ECG monitoring functions of electrodes 102/104 alternate over a set period of time as explained in greater detail elsewhere herein.

In some embodiments, electrical pulses 330 are generated as modulated bursts of short pulses. In some embodiments, a single burst comprises between 5-25 pulses, 10-20 pulses or 13-16 pulses. In some embodiments, a pulse duration is between 0.10-0.60 mS, 0.20-0.55 mS or 0.30-0.50 mS. In some embodiments, 1-3 bursts are applied during the inhalation phase of the respiratory cycle.

In some embodiments, and as shown in FIG. 3C, information regarding the respiratory cycle is derived from a respiration monitor such as, for example, a nasal pressure sensor or a nasal thermistor placed adjacent nostrils of a subject.

In some embodiments, expansion of the chest cage temporarily increases the body girth, among others, at the waistline level applying tension on band 106. Such tension strains PE sensor 508 that emits electrical signals indicating chest cage expansion or inhalation. The inhalation phase 375 is a period of time during which the pressure on abdominal organs (e.g., the stomach) is greatest as a result of expansion of the diaphragm and the chest cage.

In exhalation the process is reversed and since band 106 is axially non-extendable and non-compressible or rigid, chest cage contraction reduces the girth of the body at the waist level and exerts compressive forces on band 106, which is expressed by generation of a negative (inverted) electrical signal from PE sensor 508. Processor 202 is configured to identify the signals emitted by PE sensor 508 communicated to processor 202 and identify signals associated with the inhalation phase 375 of the respiratory cycle 322 (FIG. 3C). Once identified, processor 202 switches electrodes 102/104 to EPG mode of operation which, in turn, generate pulse bursts that affect the abdominal muscles.

As shown in the exemplary embodiment depicted in FIG. 3A, processor 202 switches (activates) electrodes 102/104 into EPG mode of operation to generate pulse 330 bursts 332 at or just prior to onset of inhalation phase 375 and switches (inactivates) electrodes 102/104 into ECG mode of operation at or just after end 390 of inhalation phase 375.

Additionally, or alternatively, electrical device 100 comprises an ECG monitor 406 configured to communicate ECG signals 320 to processor 202 that provide information not only regarding phases of the respiration cycle (i.e., inhalation/exhalation) but also predict the time of onset 350 of the inhalation phase at which treatment of the digestive tract is most effective. In some embodiments and as explained in greater detail elsewhere herein, electrodes 102/104 are configured to receive ECG signals.

As explained elsewhere herein, processor 202 is configured to run an algorithm for identifying the respiration waveform and phase derived from ECG signals e.g., ECG-derived respiration (EDR). In some embodiments, the processor runs an algorithm for identifying the respiration waveform extrapolated from ECG R-R intervals.

The EDR (ECG-Derived Respiration-A technique to obtain a respiration signal from an ECG) technique is based on ECG QRS pattern: variation in the heart rate, variation in the R peak amplitude and in the QRS area.

As shown in FIG. 3B, in some embodiments, pulse duration is 0.2 mS and the gap duration 395 between pulses is approximately 28 mS (burst duration is approximately 450 mS and the gap between bursts can vary between 0 mS to 1000 mS). In one embodiment ECG samples can be taken in between pulses (in a rate of, for example, 1 KHz.) While the switching system disconnects the ECG circuit shortly before the pulse and reconnects it shortly after the pulse (Switch to EPG mode before pulse and back to ECG mode after the pulse). In this configuration only about 0.1-0.2% of samples are missed (FIG. 3B, 325). Nevertheless, the detection of heartbeat is not affected.

In some embodiments and as depicted in FIG. 3C, processor 202 synchronizes the generated bursts such that the bursts are generated in between predicted consecutive heart beats as well as during the inhalation phase 375 of the respiratory cycle. In this configuration, processor 202 switches to ECG mode of operation about 10-100 mS after a burst and back to EPG mode of operation shortly before the next heartbeat. In transition from EPG to ECG the electrodes are shorted for a duration of 0.5 mS to 2 mS, in order to discharge the electrodes.

Disconnecting the ECG circuit from the electrodes and discharging the electrodes is carried out for the purpose of protecting the ECG circuit from the high voltage stimulation signal. As explained elsewhere herein, in some embodiments, electrodes 102/104 are dual function (e.g., EPG/ECG monitoring) electrodes rendering the electrodes incapable of ECG sampling during the EPG mode of operation.

A potential advantage of acquisition of a full ECG reading 320/320-1 throughout the full respiratory cycle 322 is in that it provides processor 202 an accurate ECG database for EDR analysis and to accurately identify phases and portions of phases at every point along the respiratory cycle.

A potential advantage in accurate identification of accurate points of phases of the respiratory cycle is in that processor 202 is able to accurately identify a point of onset of inhalation phase 375 and synchronize the application of electric pulse bursts 332 accordingly to a point in the respiratory cycle at which stimulation treatment of the digestive tract is most effective.

In some embodiments, processor 202 is in communication with one or more electrical switches device that switch electrodes 102/104 from an ECG mode of operation to an EPG mode of operation and vice versa. For example, when the switches are in a closed position, electrodes 102/104 are switched to an ECG mode of operation to receive ECG signals 320. Alternatively, when the switches are in an open position, electrodes 102/104 are switched to an EPG mode of operation and are placed in communication with a Biphasic pulse generator and a DC/DC converter booster (e.g., 120 VDC 410 booster) and generate stimulating pulses 330.

A potential advantage in this configuration is in that in some embodiments, processor 202 is configured to switch a mode of operation of electrodes 102/104 between an ECG mode of operation and acquire ECG signals 320 and an EPG mode of operation and generate bursts 332 of electrical pulses 330. A potential advantage of this configuration is in that processor 202 is configured to switch electrodes 102/104 to an ECG mode of operation in between bursts 332 of pulses 330 and/or in between individual pulses 330.

In some embodiments, processor 202 is configured to control and adjust parameters of pulses 330 generated by electrodes 102/104, e.g., frequency and/or form of burst (pulse amplitude, voltage, current and others). In some embodiments, electrodes 102/104 are electrically discharged between an ECG mode of operation and an EPG mode of operation.

In some embodiments and as shown in FIG. 3C, device 100 processor 202 is configured to switch electrodes 102/104 from an ECG mode of operation to acquire ECG signals 320 to an EPG mode of operation to generate bursts 332 of electrical pulses 330 at periods of time during which at least the following conditions coexist: the respiratory cycle 322 is at the inhalation phase 375 and the ECG is in between heart beats, i.e., QRS complexes.

According to some embodiments of the invention, the electrical pulses 330 of the device 100 are defined by the following parameters: frequency between 25 and 40 Hz. In some embodiments, the frequency is 35 Hz. In some embodiments, the pulses are biphasic. In some embodiments, duration of a pulse is between or between 0.35 mS and 0.50 mS. In some embodiments, duration of a biphasic pulse is 0.45 mS. In some embodiments, there is a gap of 28 mS between pulses 330. In some embodiments, electrodes 102/104 are configured to electrically discharge during the gap 395 of 28 mS before switching to ECG mode of operation. In some embodiments, the electrical pulse 330 potential is between 100V and 140V or 110V and 130V. In some embodiments, the electrical pulse 330 potential is 120V.

Figure 4:
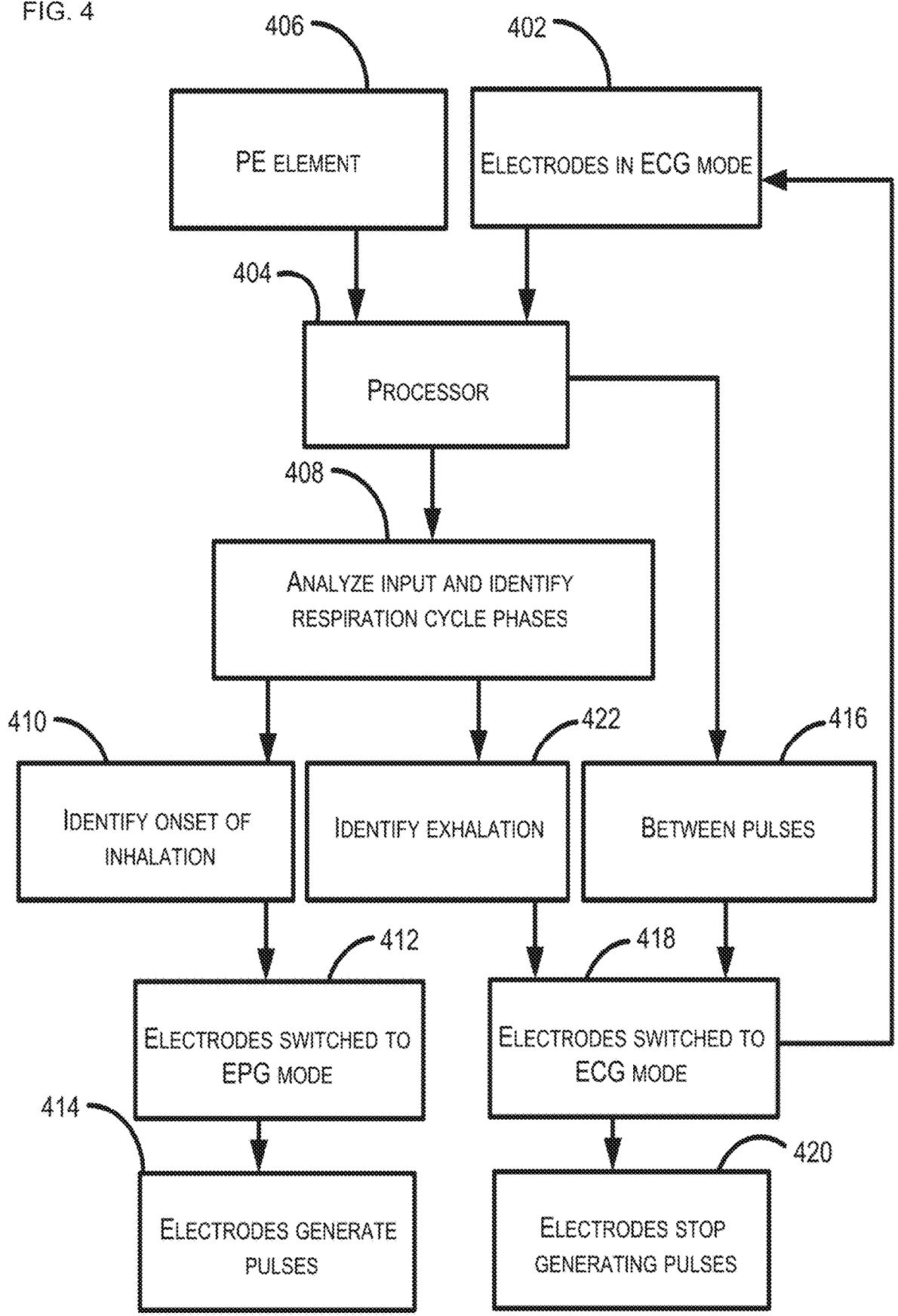
FIG. 4 is a simplified electrical flow chart of the device operation in accordance with some embodiments of the invention.

Reference is now made to FIG. 4, which is a simplified flow chart of electrical device 100 operation in accordance with some embodiments of the invention. As shown in the exemplary embodiment depicted in FIG. 4 at block 402, electrodes 102/104 are in an ECG mode of operation and configured to receive ECG signals. ECG signals from electrodes 102/104 is communicated to processor 202 in block 404. PE sensor 508 (Block 406), concurrently or consecutively communicates signals to processor 202 associated with variation in the body girth during the respiratory cycle. Processor 202 at block 408 analyzes received input from electrodes 102/104 and PE sensor 508 and identifies the respiratory cycle phases based on the received input. At block 410 processor 202 determines onset of inhalation phase 375 of the respiratory cycle 322 and switches electrodes 102/104 at block 412 from the ECG mode of operation (block 402) to an EPG mode of operation at which time electrodes 102/104 generate stimulating pulses 330 at block 414. Following generation of stimulating pulses 330, and/or in-between individual pulses (block 416) as explained in detail elsewhere herein, processor 202 switches electrodes 102/104 at block 418 from the EPG mode of operation (block 412) back to an ECG mode of operation at block 402, thus stopping generation of electrical pulses 330 (block 420).

At identification of an exhalation phase 380 of the respiration cycle 322 at block 422 PE sensor 508 processor 202 switches electrodes 102/104 at block 418 from the EPG mode of operation (block 412) back to an ECG mode of operation at block 402, thus stopping generation of electrical pulses 330 (block 420).

Reference is now made to FIG. 5A which is a cross section and a plan view of the device PE sensor mounted on an interconnecting band, and FIGS. 5B, 5C, 5D and 5E, which are cross-section view simplified illustrations of the device PE sensor in accordance with some embodiments of the invention. As shown in the exemplary embodiment depicted in FIGS. 5A, 5B and 5C, a device 500 comprises a Piezoelectric (PE) sensor 508 mounted on a mount 550. In some embodiments, mount 550 comprises an elastic PE base 509 coupled to one or more cantilevers 512. In some embodiments, elastic PE base 509 is made of metal and/or a polymer.

In some embodiments, PE mount 550 is coupled to an axially non-extendable and non-compressible band 106. Band 106 interconnects PE sensor 508 mount 550 and electrode base 112, so that motion of electrode base 112 in respect to mount 550 effects bending forces via band 106 onto mount 550 PE base 509 deforming Piezoelectric sensor 508. In some embodiments, band 106 connects PE sensor 508 to other portions of device 500, e.g., strap 206.

Tensile and compressive forces effected on mount 550 as a result of expansion and contraction of the chest rib cage, the abdominal cavity and mainly diaphragm translate to bending forces acting on mount 550 effecting deforming forces on PE element in accordance with the respiration cycle 322. Deformation of PE sensor 508 generates electrical signals to processor 202.

According to some embodiments and as shown in FIG. 5A, a portion of band 106 can move back-and-forth within housing 502 In association with the phases of the respiratory cycle.

In some embodiments and as shown in FIGS. 5B and 5C, the Piezoelectric sensor 508 base 509 is coupled to mount 550 which is coupled to band 106. For purposes of explanation only, mount 550 in the exemplary embodiments depicted in FIGS. 5B and 5C is coupled to a stationary point 555.

As shown in FIG. 5B, when band 106 moves towards the housing 502 in a direction indicated by arrow 575, band 106 effects a force moment in a direction indicated by arrow 577 effecting a bending force on base 509 and bending base 509 (e.g., away from the body wall 580 of the subject) and deforming PE sensor 508. Deformation of PE sensor 508 generates an electrical signal in a first polarity. As shown in FIG. 5C, when band 106 effects tensile forces in a direction away from housing 502 as indicated by arrow 595 it effects a bending force on mount 550, bending base 509 in an opposite direction (e.g., towards the body wall 580 of the subject). Bending, base 509 brings PE sensor 508 to deform in an opposite direction (e.g., towards the body wall 580 of the subject) and generate an electrical signal in a second, opposite polarity.

Since movement of band 106 is associated with the respiratory phase of the subject, the polarity of electrical signals generated by PE sensor 508 is associated with the respiratory phase of the subject (the direction in which PE sensor 508 is deformed by base 509).

In some embodiments, processor 202 is configured to combine information from Piezoelectric sensor 508 communicated to processor 202 with ECG information communicated to processor 202 electrodes 102/104 and generate an accurate identification of every point along the respiratory cycle e.g., the point of onset of inhalation phase 375 at which the effect on abdominal muscles and stomach is most effective. According to some embodiments, processor 202 is configured to synchronize between the electrical pulses and the respiration cycle phase identification In addition to variation of the girth of the body during the respiratory cycle, in some embodiments, expansion and contraction of the chest rib cage, the abdominal cavity and mainly diaphragm vary the spatial position of electrodes 102/104 in respect to each other. FIGS. 5D and 5E depict a change in spatial position of electrode base 110 in respect to electrode base 112 during an inhalation phase of a subject. In the exemplary embodiments depicted in FIGS. 5D and 5E, electrode base 110, being positioned more anteriorly on the body of the subject than electrode base 112 as shown in FIG. 2.

FIG. 5D illustrates device 500 placed on a subject during exhalation at which time electrodes 102/104 respective bases 110/112 are generally on a same plain of body wall 580 of a subject. During inhalation, and as shown in FIG. 5E, radial movement of electrode base 110 in a direction depicted in FIG. 5E by arrow 525 is greater in electrode base 110 than in electrode base 112. This results in electrode bases 110/112 being on different plains in the end of inhalation phase 375.

The difference in the spatial position of electrode base 110 in respect to electrode base 112 exerts deforming forces (e.g., bending and/or shearing forces) on mount 550 deforming PE sensor 508 as explained in greater detail elsewhere herein.

Reference is now made to FIGS. 6A, 6B and 6C which is an exploded view and plan view simplified illustrations of the device and electrode skin-contact surfaces in accordance with some embodiments of the invention. In some embodiments, the relative distance and/or the relative angle between the electrodes 102/104 are is adjustable. As shown in FIGS. 6A, in some embodiments, electrodes 102/104 comprise a back surface 616 and a skin-contact side 620 coated with a biocompatible conductive hydrogel 628 configured to adhere to skin. In some embodiments, back surface 616 comprises one or more couplers 622/624 configured to couple electrodes 102/104 to electrode bases 110/112 respectively.

In some embodiments, at least one of couplers 622/624 is configured to conduct electrical pulse energy from a device 100 pulse generator (not shown) to the electrode skin-contact surface 620 and/or ECG signals from skin-contact surface 620 to processor 202. Additionally, or alternatively, in some embodiments, one of coupler 622/624 is configured to conduct pulse energy from a pulse generator (not shown) to an electrode skin-contact surface and/or ECG signals from skin-contact surface 620 to processor 202 and the other is electrically insolated and serves as an anti-rotation coupler.

In some embodiments the standard metallic spring male couplers 622&624 of TENSE/ECG electrodes are replaceable by a pair of conductive magnetic studs. The magnetic male studs attract to female snaps that are mounted into the plastic base 112 maintaining proper mechanical and conductive coupling. Since in order to connect the electrodes to the device there is no need to press the coupler this feature enable comfort and easy coupling. It also enables easy removal of the device from the body and placing the device back ensuring good contact with the electrodes without pilling off the electrodes from the skin, overcoming a technical problem of pressing a device to electrodes when the electrode is placed on soft skin.

To avoid "hot spot", the studs are secured to the electrodes by means of an conductive Carbon coated eyelet 626.

In some embodiments, the device comprises an electrode rotation mechanism 608 comprising a polygonal rotatable nut 610 to which back surface 606 one or more couplers 622/624 is fitted. In some embodiments, polygonal rotatable nut 610 is configured to rotate and allow rotational positioning of electrodes 102/104 in a plurality of orientations in respect to band 106. A potential advantage in the rotatability of electrodes 102/104 is in that the electrodes are adjustable, to provide the most effective response of the digestive tract and primarily the esophagus and stomach, to device 100 activity. In some embodiments, couplers 622/624 are electrically conductive and are configured to conduct pulse energy from device 100 to the electrode skin-contact surface 620 and/or ECG signals from skin-contact surface 620 to processor 202.

In some embodiments, electrodes 102/104 are structurally similar to electrodes used for transcutaneous electrical nerve stimulation (TENS). For example, having a layered structure comprising (from the back surface 616 to skin-contact surface 620) a durable topcoat woven material, a conductive layer, e.g., silver filled polymer, a conductive carbon film, a hydrogel layer and siliconized release liner.

In some embodiments, mechanism 608 of the band 106 comprises a matching washer 612 that accommodates a collar 614 for securing strap 206 to the band 106 and electrode 102 base 110. Collar 614 is pivotably coupled to band 106 so that to maintain strap 206 aligned with band 106.

In some embodiments, the device 600 comprises a securing cap 616 having a left-handed thread for securing the cap 616 to second end 606 of the band 106.

Figure 7B:
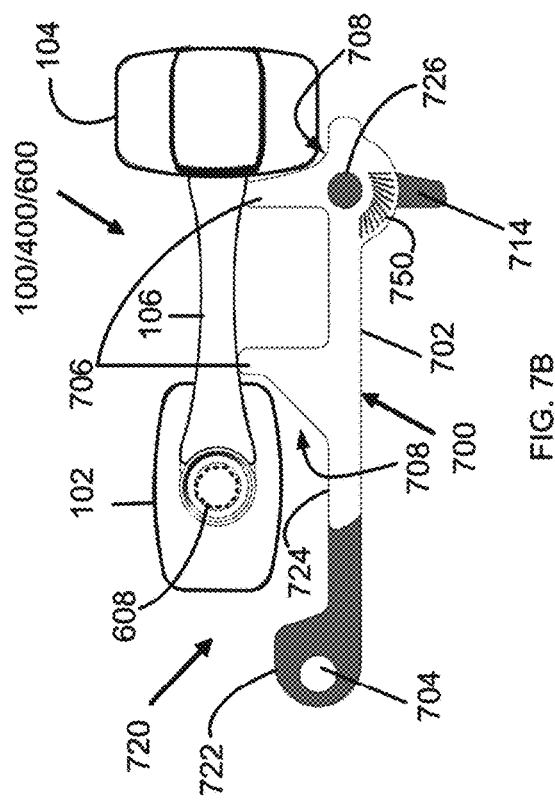
FIGS. 7A, 7B and 7C are plan view simplified illustrations of a positioner for the device positioner in accordance with some embodiments of the invention.
Figure 7A:
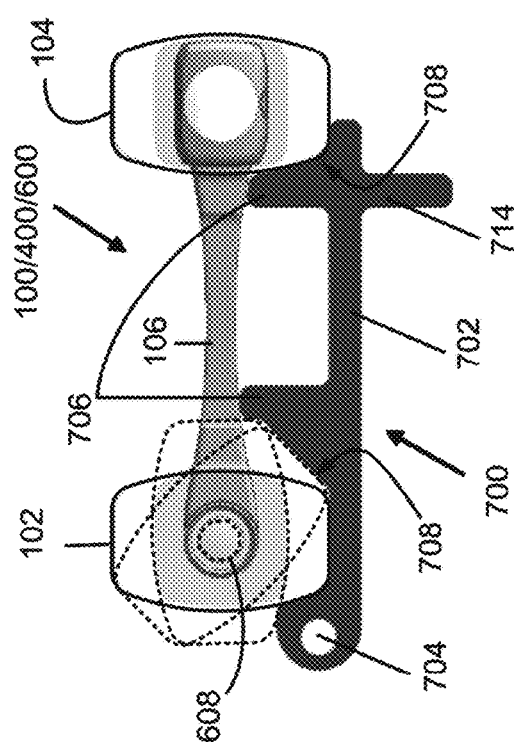
Figure 7C:
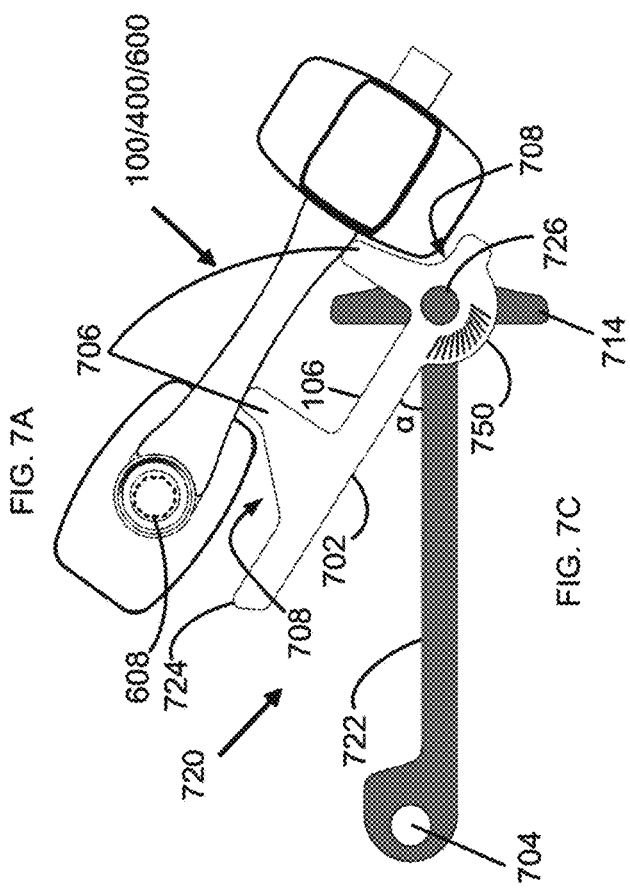

Turning to FIGS. 7A, 7B and 7C, collectively referred to as FIG. 7, which are plan view simplified illustrations of the device and a positioner in accordance with some embodiments of the invention. As shown in FIG. 7, in some embodiments, a positioner 700 is sized and fitted to position electrical device (e.g. 100/400/600) on the body of a user. In some embodiments, positioner 700 is used to position the device 100/400/600 in a predetermined location relative to the navel of a user. As shown in the exemplary embodiment depicted in FIG. 7, positioner 700 comprises a positioner body 702, a navel locator aperture 704 disposed at one end of body 702, a one or more band 106 supports 706 protruding from body 702, one or more electrode accommodating cutouts 708 and one or more handles 714 extending from body 702 in a direction opposite to band 106 supports 706. Cut outs 708 are shaped to support rotation of one or both electrodes 102/104 via polygonal rotatable protrusion 608 as depicted, e.g., for electrode 102 in FIG. 7A by phantom lines. In some embodiments, the positioner 700 is flat. In some embodiments, positioner 700 is extendable to fit the body of different users. In some embodiments, the positioner 700 is contoured to fit the body of different users. In some embodiments, the positioner 700 is flexible to fit around the body of different users.

Positioner 700 is configured to serve as a baseline positioning device, i.e., positioning electrodes 102/104 at locations found empirically to be most effective for both ECG signal acquisition and electrical pulse generation (EPG). In some embodiments and as shown in the exemplary embodiments depicted in FIGS. 7B and 7C, positioner 720 comprises a pivotally coupled baseline positioning arm 722 and a device 100/400/600 carrier arm 724. In some embodiments, positioner 720 comprises a protractor 750 located about a pivot hinge 726 coupling baseline positioning arm 722 and device 100/400/600 carrier arm 724.

For most effective digestive tract treatment, device 100/400/600 is placed at a baseline location on the body of a user by placing positioner 720 such that aperture 704 is placed about the umbilicus (navel) of the user. This is followed by pivoting device 100/400/600 carrier arm 724 in respect to baseline positioning arm 722 until optimal responses are achieved (e.g., strongest ECG signal generation and/or most effective electric pulses are generated) and angle (a) as defined by protractor 750 is recorded per the specific user. A final positioning step comprises pivoting one or more electrodes 102/104 until acquisition of optimal responses is achieved thus finalizing the positioning of device 100/400/600. At this stage electrodes 102/104 are attached to the skin (e.g., by removal of a peel-off film to expose the adhesive surface) and positioner 720 removed.

Experimental Results

As explained elsewhere herein, ECG-derived respiration (EDR) algorithm is employed to obtain information regarding the respiration cycle and phases thereof (i.e., inhalation and expiration). FIGS. 8A, 8B 9A, 9B, 10, 11A, 11B, 12A and 12B are graphs depicting EDR and piezoelectric sensor results obtained during experiments carried out by the authors of this disclosure demonstrating the correlation between various obtained elements of the ECG input and the respiratory cycle and generation of trigger points (i.e., electrical pulse electrode activation points) correlated with onset of the inhalation phase of the respiratory cycle.

Figure 8A:
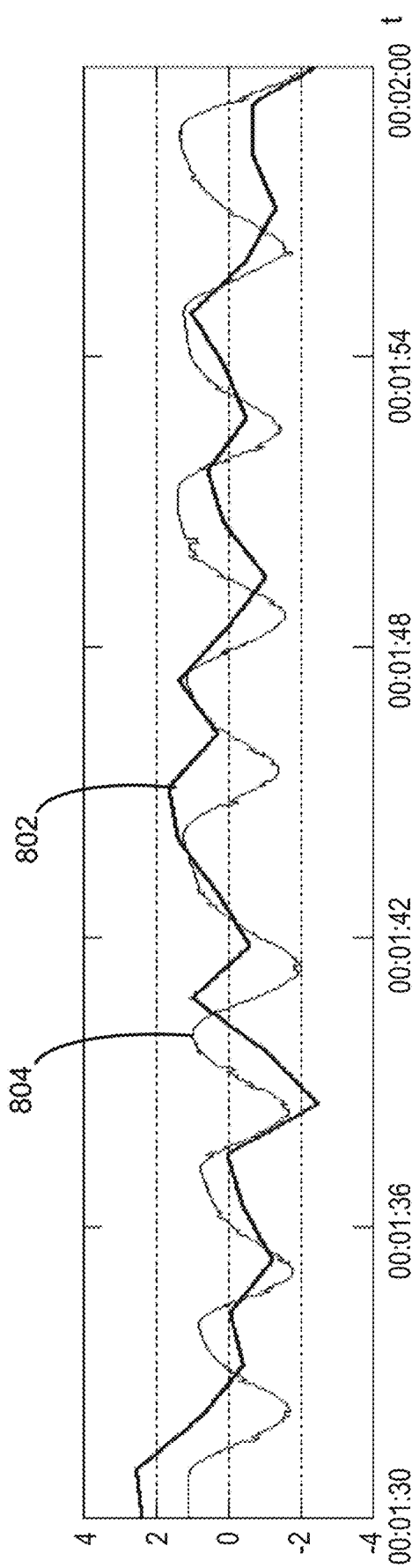
FIGS. 8A and 8B are graphs depicting EDR obtained pulse rate alteration and R-peak amplitude in correlation with reference respiratory cycle signal in accordance with some embodiments of the invention.

FIG. 8A depicts heart pulse rate input 802 that represents the duration between consecutive heart beats (e.g., R-R interval) drafted against a reference signal 804 produced by a respiration monitor such as, for example, a nasal pressure sensor or a thermistor placed adjacent nostrils of a subject. The graph depicted in FIG. 8A shows correlation between the heart pulse rate input 802 and reference signal 804.

Figure 8B:
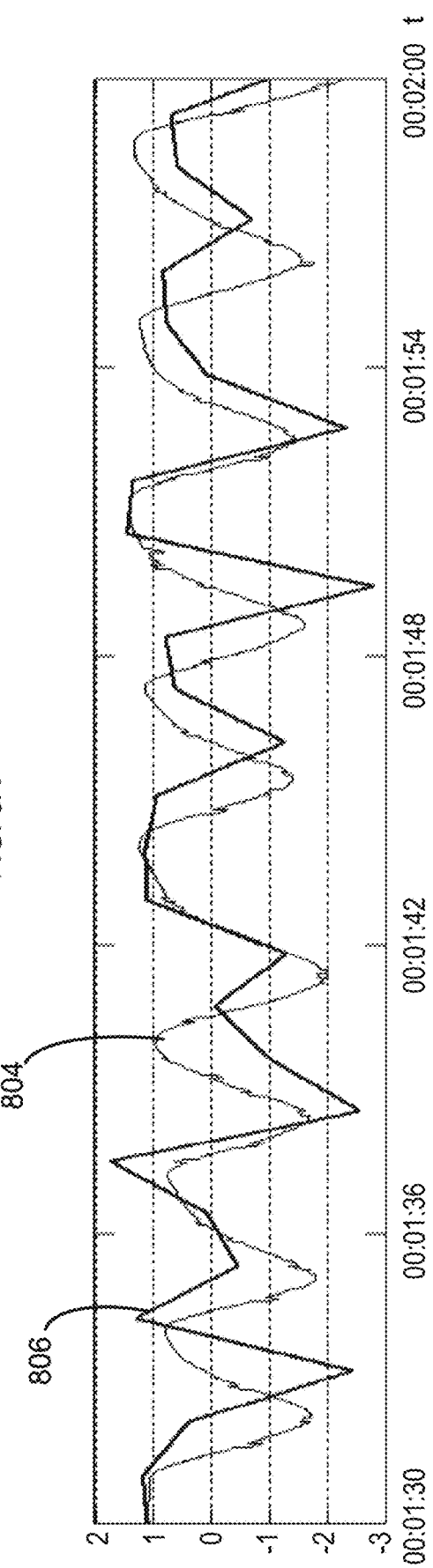

FIG. 8B depicts R peak amplitude 806 drafted against reference signal 804 produced by a respiration monitor such as, for example, a nasal pressure sensor or a thermistor placed adjacent nostrils of a subject. The graph depicted in FIG. 8B shows correlation between the R peak amplitude 806 and reference signal 804.

Figure 9A:
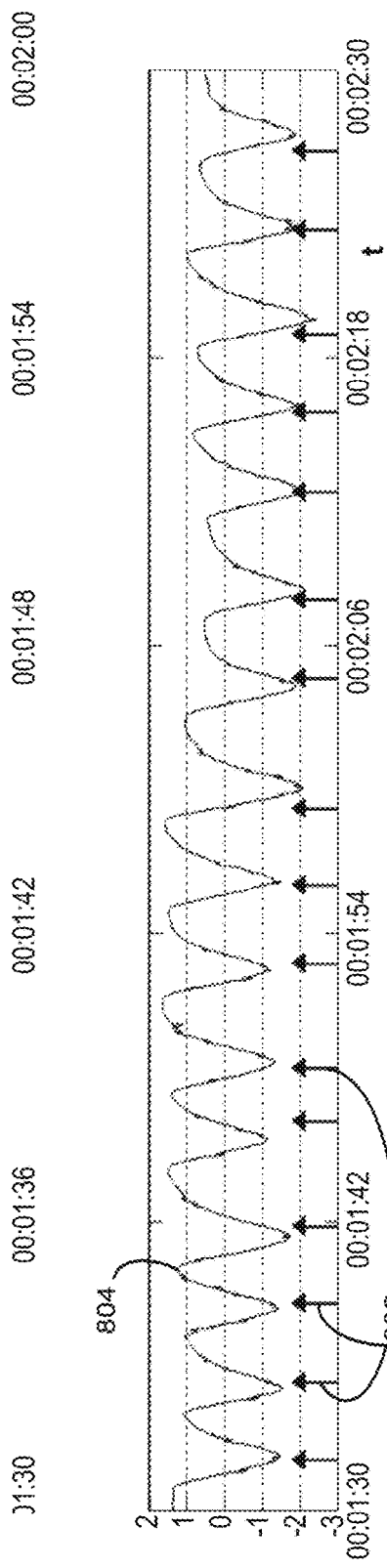
FIGS. 9A, 9B and 9C are graphs depicting EDR obtained processor pulse generation trigger points based on the pulse rate alteration (FIG. 9A), R-peak amplitude (FIG. 9B) and a combination of the two algorithms thereof (FIG. 9C) drafted against reference respiratory signal measured by a nasal flow sensor thermistor in accordance with some embodiments of the invention.

The graph shown in FIG. 9A demonstrates processor generated trigger points 902 based on the heart pulse rate input 802 drafted against reference signal 804 produced by a respiration monitor such as, for example, a nasal pressure sensor or a thermistor placed adjacent nostrils of a subject. In some embodiments, electrical device 100 processor 202 is configured to activate electrodes 102/104 at generated trigger points 902 as shown in FIG. 9A to generate electrical pulses as explained in detail elsewhere herein.

Figure 9B:
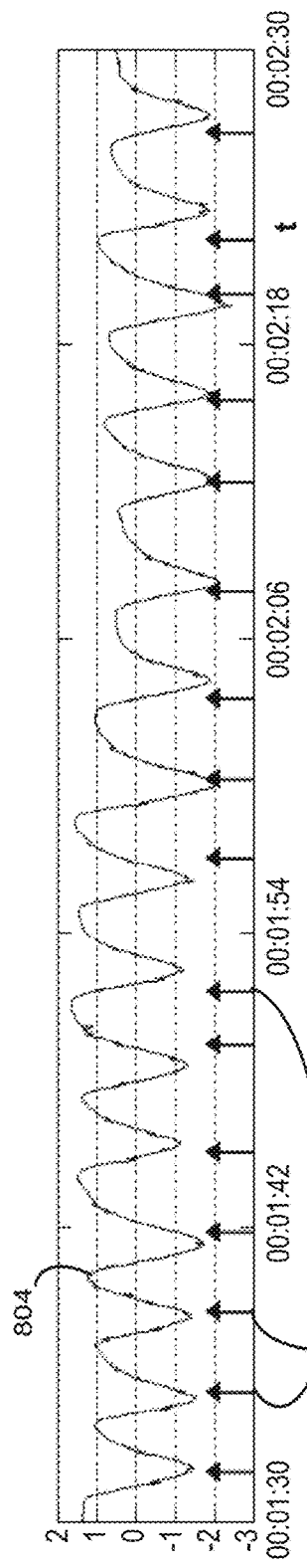

Similarly, to the graph shown in FIG. 9A, the graph shown in FIG. 9B demonstrates processor generated trigger points 904 based on the R peak amplitude 806 drafted against reference signal 804 produced by a respiration monitor such as, for example, a nasal pressure sensor or a thermistor placed adjacent nostrils of a subject. In some embodiments, electrical device 100 processor 202 is configured to activate electrodes 102/104 at generated trigger points 904 as shown in FIG. 9B to generate electrical pulses as explained in detail elsewhere herein.

Figure 9C:
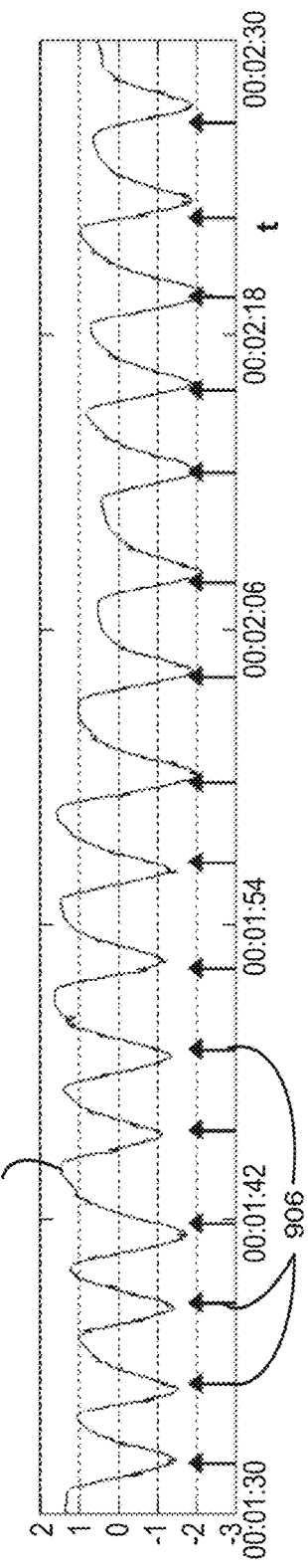

The graph shown in FIG. 9C demonstrates processor generated trigger points 906 based on a combined input from heart pulse rate input 802 and R peak amplitude 806. In some embodiments, electrical device 100 processor 202 is configured to activate electrodes 102/104 at generated trigger points 906 as shown in FIG. 9C to generate electrical pulses as explained in detail elsewhere herein.

The graphs shown in FIGS. 9A, 9B and 9C depict processor 202 generated trigger points 902/904/906 positioned in correlation with onset of the inhalation phase 375 of the respiratory cycle 322.

Figure 10:
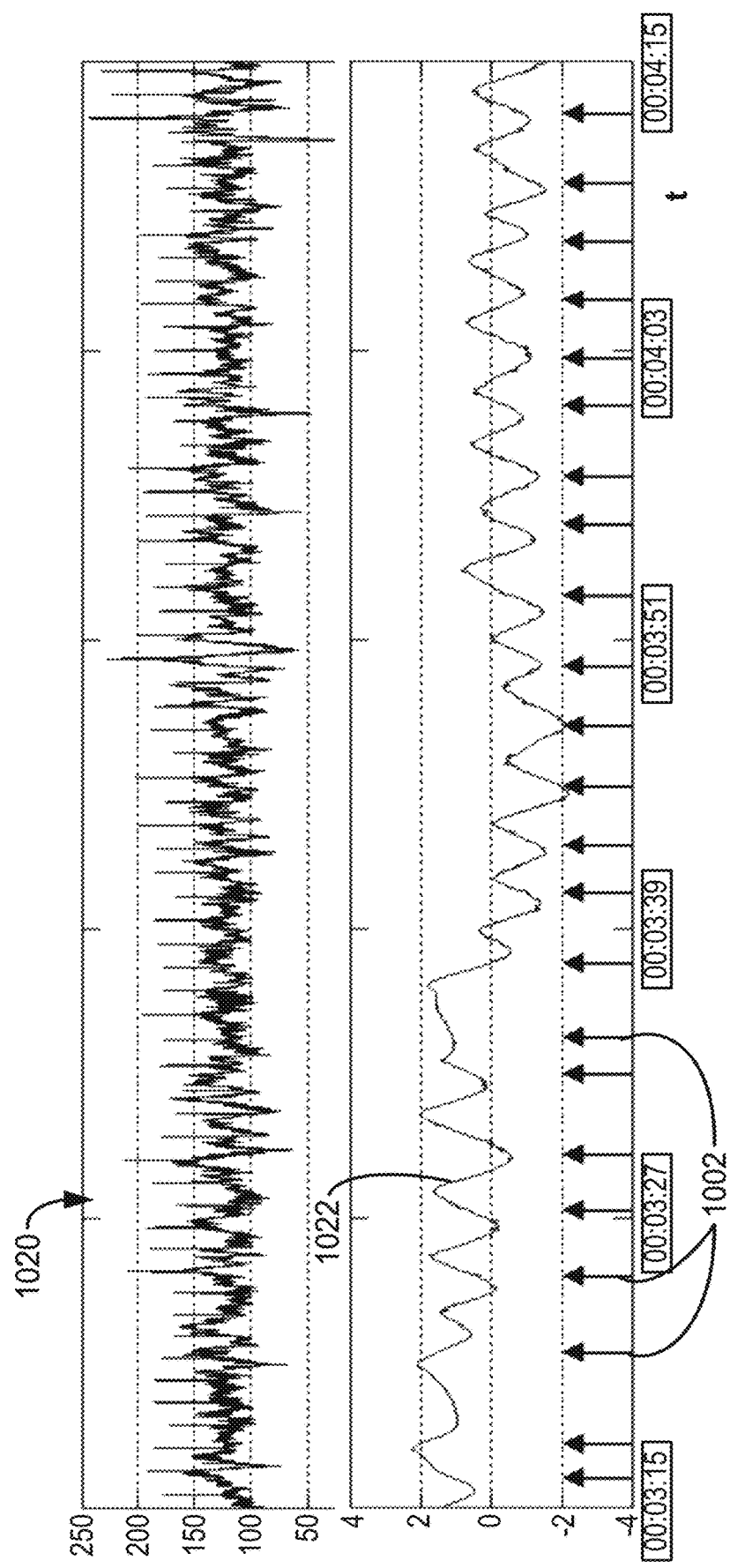
FIG. 10 is a graph of exemplary EDR triggers obtained with background interference of the data generated while movement of the subject.

Reference is now made to FIG. 10, which is a graph of exemplary EDR triggers obtained with background interference of the data generated by movement of the subject. As shown in FIG. 10, the ECG-derived respiration (EDR) algorithm employed to obtain information regarding the respiration cycle and phases thereof (i.e., inhalation and expiration) is configured to overcome "noise" interference and movement of the subject during the treatment period and generate trigger points 1002. In some embodiments, electrical device 100 processor 202 is configured to activate electrodes 102/104 at generated trigger points 1002 as shown in FIG. 10, correlated with onset of the inhalation phase of the respiration cycle to generate electrical pulses as explained in detail elsewhere herein. The generated respiratory cycle 1022 and trigger points 1002 are shown in FIG. 10 in correspondence with the ECG reading 1020 from which the EDR data was obtained.

Figure 11A:
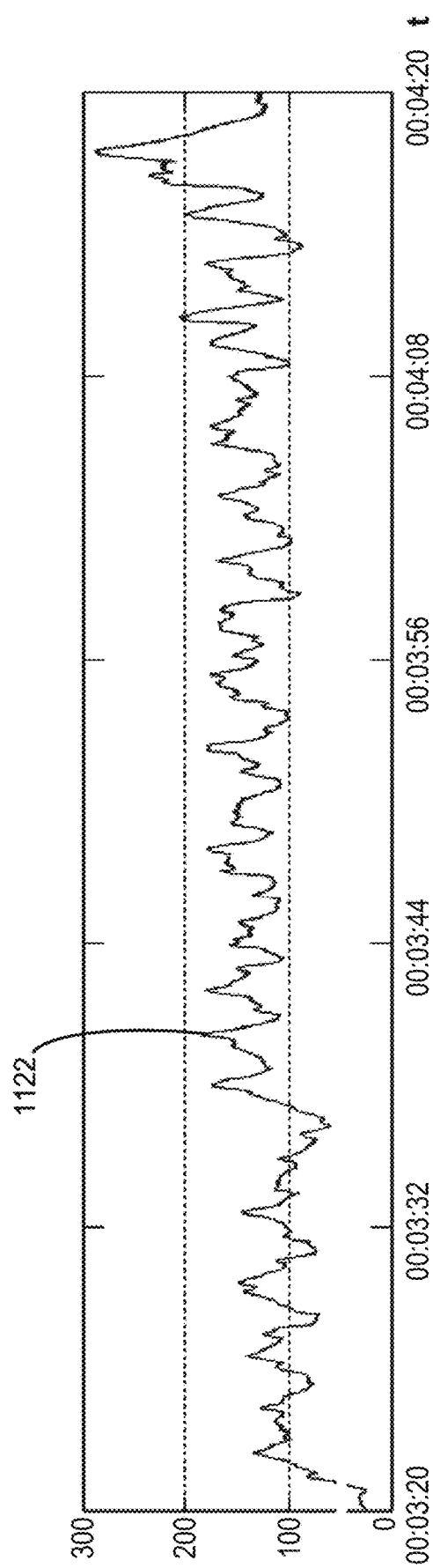
FIGS. 11A and 11B are graphs of the respiratory cycle on obtained signals from PE element sensor in movement and obtained signals from PE element sensor passed through a low pass 2 Hz filter.
Figure 11B:
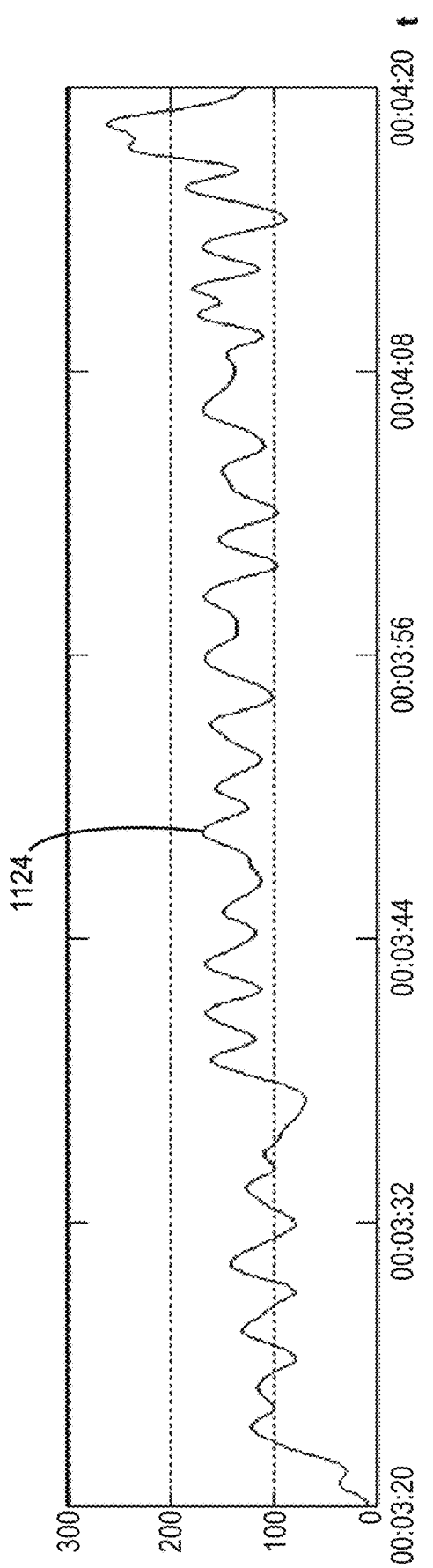

FIG. 11A, which is a graph of the respiratory cycle 1122 generated by processor 202 based on obtained signals from PE sensor 508 as explained in detail elsewhere herein. FIG. 11B, depicts a graph of the respiratory cycle 1124 generated by processor 202 based on obtained signals from PE sensor 508 as explained in detail elsewhere herein and passed through a low pass 2 Hz filter.

FIGS. 12A and 12B depict trigger positions obtained from input from piezoelectric element sensor 508 in rest (12A) and during user movement (12B) as explained elsewhere herein. FIG. 12A depicts a graph of triggers 1202 in correlation with respiratory cycle 1222 at rest. FIG. 12B, depicts a graph of triggers 1204 in correlation with the respiratory cycle 1224 generated by processor 202 based on obtained signals from PE sensor 508 with background interference of the data generated by and movement of the subject. As shown in FIG. 12B, the device 100 processor 202 is configured to activate electrodes 102/104 at generated trigger points 1204 as shown in FIG. 12B, correlated with onset of the inhalation phase (ascending portion of the graph) of the respiration cycle as obtained from the PE element to generate electrical pulses as explained in detail elsewhere herein.

Figure 13:
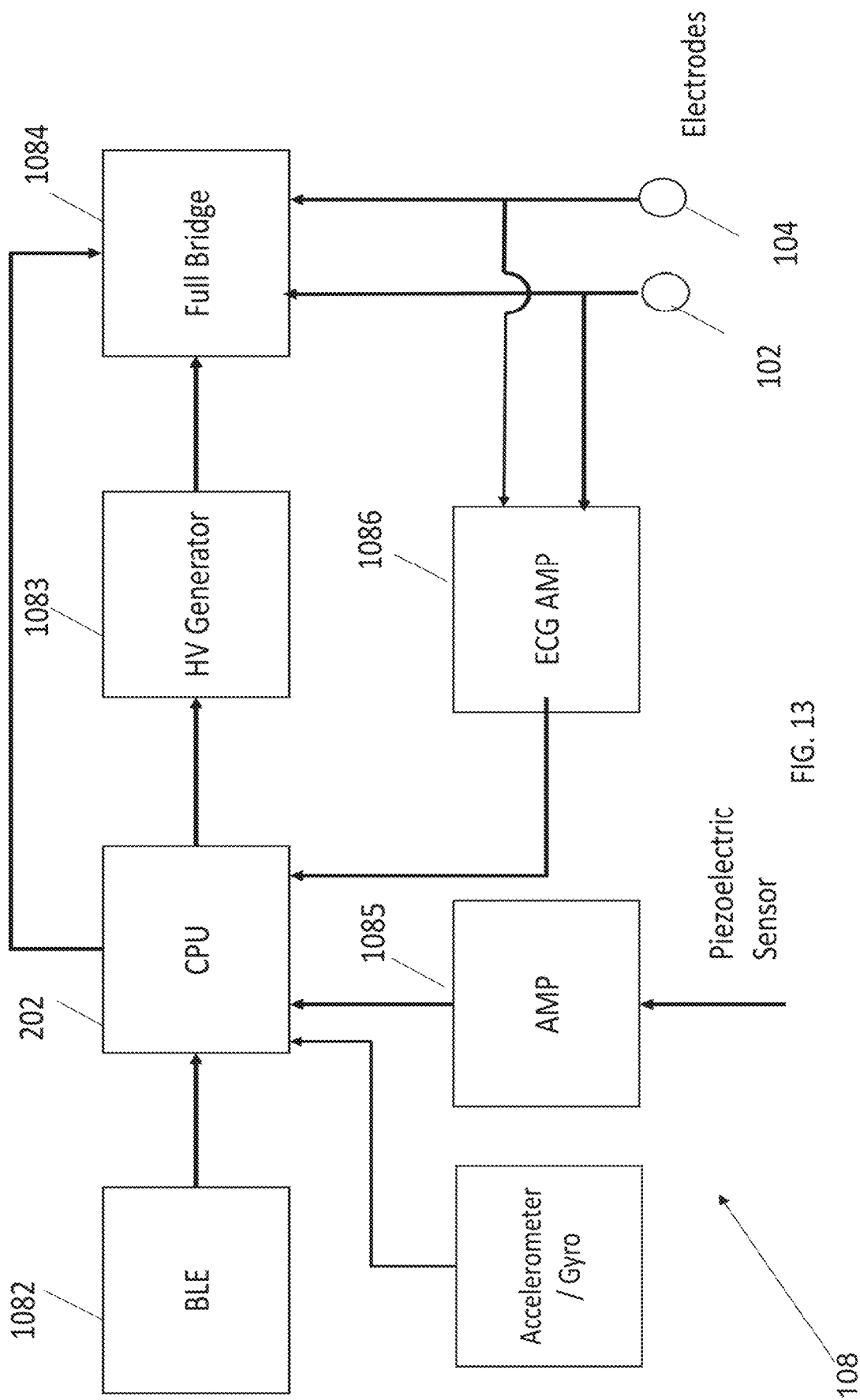
FIG. 13 is a view simplified illustration of the control unit, in accordance with some embodiments of the disclosed subject matter.

FIG. 13 is a view simplified illustration of the control box in accordance with some embodiments of the disclosed subject matter. Control box 108 includes CPU (processor) 202, BLE (Bluetooth Low Energy) 1082, High Voltage Generator 1083, full bridge unit 1084, Piezo AMP 1085, ECG AMP 1086 and electrodes 102/104.

The CPU 202 is configured for controlling the device. According to some embodiments the CPU 202 transmits and receives data and commands via the BLE 1082 which communicates with the application. The application is explained in greater details in FIGS. 14A, 14B, 14C and 14D. The CPU 202 also controls the High Voltage Generator 1083.

The High Voltage generator 1083 is configured for applying current on the electrodes 102/104. The High Voltage generator 1083 may generate up to about 120 Volt and is connected to a full bridge unit 1084.

The full bridge unit 1084 is configured for switching the current in sequence to and between the electrodes 102/104. The full bridge unit 1084 is controlled by the CPU 1081.

The electrodes 1087 are connected also to ECG amplifier 1086. And are configured for being placed over the human body for monitoring ECG and respiration and for stimulating.

The ECG amplifier 1086 is configured for amplifying and filtering the ECG signals and for transmitting its output of the electrodes 102/104 to the CPU 1081.

The Piezo Amplifier 1085 is configured for filtering noises from the Piezo and for amplifying the Piezo signal.

According to some embodiments the device includes one or more accelerometer sensor electrically connected to the CPU and provide information of body position and movement (not shown in the figure).

FIGS. 14A, 14B, 14C, 14D and 14E illustrates exemplary screen shots of an application for operation, control and physiological parameters report of the disclosed device. According to some embodiments the device may be controlled by the application. According to some embodiments the application collects data related to the user and/or to the device.

Figures 14A, 14B, 14C:
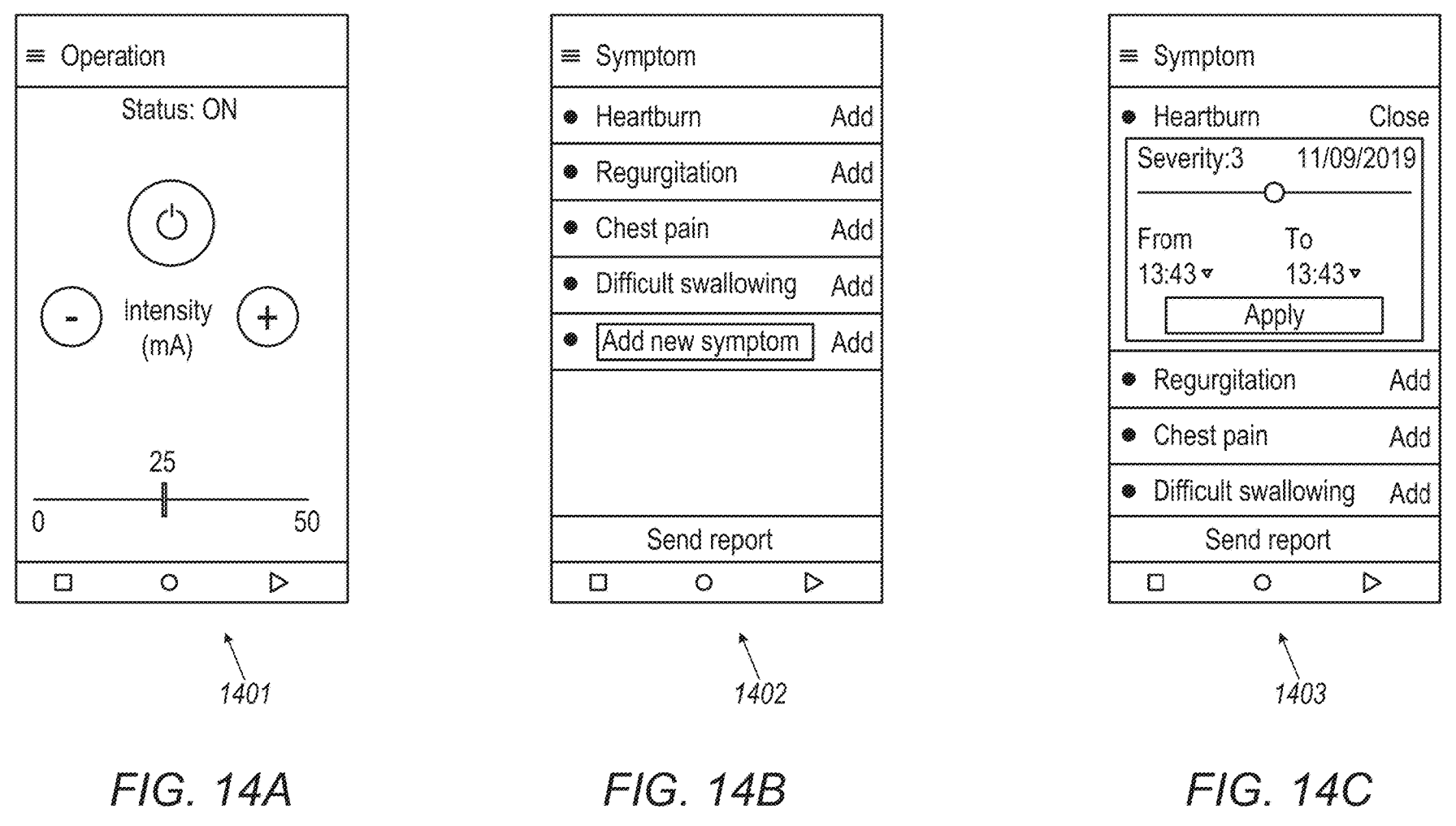

FIG. 14A illustrates an application screen shot 1401 for controlling the device. Screen 1401 enables a user to turn the stimulation On and Off via a touch screen key. Screen 1401 enables a user to change the intensity of stimulation via "+" "−" touch screen keys. The application may also display error messages in the bottom area of the screen. (not shown in the figure) For example a message when the replaceable electrodes are disconnected or too dry or wear out. The Application may send to the cloud the following data related to screen 1401: time of on/off operation, changing intensity information and all the messages notes that are shown on the screen.

FIGS. 14B and 14C illustrate screen 1402 and 1403 which are associated with collecting user's data. Screen 1402 displaying user symptoms. Screen 1402 and 1403 allow the user to edit the symptoms. According to some embodiments each defined symptom includes severity and time of the event (real time or backward event, such as a night event that is reported in the morning) The defined symptoms may be sent to the cloud.

Figures 14D, 14E:

FIG. 14D illustrates screen 1404 is for collecting daily activity and for sending the activity to the cloud.

FIG. 14E illustrates screen 1405 which depicts two counters: the number of triggers for activating the stimulation according to ECG results vs. the number of triggers for activating the stimulation according to the piezoelectric sensor. Screen 1405 also provides information about the time that the device was active on each mode.

The software application may also enable to monitor heart pulse and breathing rates and to send this information to the cloud.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the application controls.

The descriptions of the various embodiments of the invention have been ed for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A non-invasive treatment device, comprising:
    a plurality of electrodes of an ECG sensor, and
    a processor, electrically connected to said electrodes,
    wherein, said processor is configured for switching at least two of said electrodes between an ECG mode in which said electrodes receive subject body signals from which said processor is configured for deriving a respiration phase, and an EPG mode, in which said electrodes generate electrical pulses configured for stimulating the abdominal muscles,
    wherein said switching from said ECG mode to said EPG mode and from said EPG mode to said ECG mode synchronizes said electrical pulses with said respiration phase, such that said simulation is applied according to said respiration phase, and
    wherein said processor is further configured for detecting from said body signals an inhalation phase, and for switching from said ECG mode to said EPG mode as a result of said detecting, such that said simulation is applied during said inhalation phase.

2. The device of claim 1, wherein said detecting comprises utilizing Electrocardiogram Derived Respiration algorithm for said detecting said inhalation phase.

3. The device of claim 1, wherein said device is further configured for treating digestive symptoms by said stimulation, wherein said digestive symptoms being one member selected from a group consisting of gastroesophageal reflux, obesity and constipation.

4. The device of claim 1, wherein said electrodes are configured for being positioned over abdominal muscles at the level of the waistline of said subject.

5. The device of claim 1, wherein said processor is further configured for synchronizing said electrical pulses for stimulating the abdominal muscles with an inhalation phase of said subject and between heartbeats to avoid loss of ECG data.

6. The device of claim 1, wherein said electrodes are dual function for operating said EPG mode and said ECG mode.

7. The device of claim 1, further comprising an ECG circuit connectable to said electrodes, wherein said switching to said EPG mode comprises disconnecting said ECG circuit from said electrodes and wherein said switching to said ECG mode comprises reconnecting said ECG circuit to said electrodes.

8. The device according to claim 1, wherein said processor is configured to switch from said EPG mode to ECG mode in between bursts of pulses.

9. The device according to claim 1, wherein said processor is configured to switch from said EPG mode to ECG mode in between pulses.

10. The device according to claim 1, wherein said device comprises one or more accelerometer or a gyro unit electrically connected to said processor; wherein said accelerometer or said gyro unit is configured to adjust the stimulation intensity according to the body position and body activity.

11. The device according to claim 1 wherein said processor is configured to measure muscles response to stimulation and adjust stimulation parameters to generate stable muscle movement.

* * * * *